United States Patent
Phanstiel, IV et al.

(10) Patent No.: US 9,346,741 B2
(45) Date of Patent: May 24, 2016

(54) POLYAMINE TRANSPORT SELECTIVE THERAPEUTIC AGENTS WITH ENHANCED STABILITY

(71) Applicants: Otto Phanstiel, IV, Oviedo, FL (US); Aaron Muth, Orlando, FL (US)

(72) Inventors: Otto Phanstiel, IV, Oviedo, FL (US); Aaron Muth, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 14/388,856

(22) PCT Filed: Mar. 14, 2013

(86) PCT No.: PCT/US2013/031166
§ 371 (c)(1),
(2) Date: Dec. 9, 2014

(87) PCT Pub. No.: WO2013/148230
PCT Pub. Date: Oct. 3, 2013

(65) Prior Publication Data
US 2015/0017231 A1   Jan. 15, 2015

Related U.S. Application Data

(60) Provisional application No. 61/616,944, filed on Mar. 28, 2012.

(51) Int. Cl.
| | | |
|---|---|---|
| *C07C 211/31* | (2006.01) | |
| *A61K 31/785* | (2006.01) | |
| *C08G 73/02* | (2006.01) | |
| *A61K 31/138* | (2006.01) | |
| *C07C 211/27* | (2006.01) | |
| *C07C 211/30* | (2006.01) | |

(52) U.S. Cl.
CPC ............. *C07C 211/31* (2013.01); *A61K 31/138* (2013.01); *A61K 31/785* (2013.01); *C07C 211/27* (2013.01); *C07C 211/30* (2013.01); *C08G 73/0206* (2013.01)

(58) Field of Classification Search
CPC .. C07C 211/31; C07C 211/30; C07C 211/27; A61K 31/138; A61K 31/785; C08G 73/0206
See application file for complete search history.

(56) References Cited

U.S. PATENT DOCUMENTS

| 8,497,398 B1 * | 7/2013 | Phanstiel, IV | C07C 211/31 564/305 |
|---|---|---|---|
| 2007/0213397 A1 | 9/2007 | Phanstiel | |
| 2009/0069441 A1 | 3/2009 | Phanstiel | |
| 2009/0155265 A1 | 6/2009 | Zeldis | |
| 2012/0015865 A1 | 1/2012 | Zelphati et al. | |

OTHER PUBLICATIONS

Wolff, Manfred E. "Burger's Medicinal Chemistry, 5ed, Part I", John Wiley & Sons, 1995, pp. 975-977.*
Kaur et al, Journal of Medicinal Chemistry, 2008, 51(5), 1393-1401.*
Wallick, C. et al., "Key role for p27Kip1, retinoblastoma protein Rb, and MYCN in polyamine inhibitor-induced G1 cell cycle arrest in MYCN-amplified human neuroblastoma cells", Oncogene, 2005, vol. 24, pp. 5606-5618.
Hibshoosh, H. J.,et al. "Effects of overexpression of ornithine decarboxylase (ODC) on growth control and oncogene-induced cell transformation", Oncogene, 1991, vol. 6, pp. 739-743.
Meyskens Jr, F., "Development of Difluoromethylornithine (DFMO) as a chemoprevention agent", Clin. Cancer Res. 1999, vol. 5, pp. 945-951.
Fabian, C et al., "A Phase II breast cancer chemoprevention trial of oral alpha-difluoromethylornithine: Breast tissue, imaging, and serum and urine biomarkers", Clin. Cancer Res., 2002, vol. 8, pp. 3105-3117.
Abeloff, M. et al., "Phase I trial and pharmacokinetic studies of alpha-difluoromethylornithine—an inhibitor of polyamine biosynthesis" J. Clin. Oncol. 1984, vol. 2, pp. 124-130.
Seiler, N., "Thirty years of polyamine-related approaches to cancer therapy. Retrospect and prospect. Part 2. Structural analogues and derivatives", Curr. Drug Targets 2003, vol. 4, pp. 537-564.
Gerner, E et al., "Polyamines and cancer: old molecules, new understanding" Nat. Rev. Cancer, 2004, vol. 4, pp. 781-792.
Phanstiel, O. et al., "Design of polyamine transport inhibitors as therapeutics", in Polyamine Drug Discovery, 1 ed.; Casero, R. W., P., Ed. Royal Society of Chemistry: 2011; p. 302.
American Cancer Society. "Cancer facts & figures", 2012, pp. 1-65.
BasuRoy, et al., "Activated K-RAS increases polyamine uptake in human colon cancer cells through modulation of caveolar endocytosis", Mol. Carcinogen., 2008, vol. 47, pp. 538-553.
Basuroy, U. et al., "Emerging concepts in targeting the polyamine metabolic pathway in epithelial cancer chemoprevention and chemotherapy", J. Biochem., 2006, vol. 139, pp. 27-33.
Covassin, L. et al.,"Synthesis of spermidine and norspermidine dimers as high affinity polyamine transport inhibitors", Bioorg. Med. Chem. Lett., 1999, vol. 9, pp. 1709-1714.
Burns, M. et al., "Amino acid/spermine conjugates: Polyamine amides as potent spermidine uptake inhibitors", J. Med. Chem., 2001, vol. 44, pp. 3632-3644.
Weeks, R. R et al., "Novel lysine-spermine conjugate inhibits polyamine transport and inhibits cell growth when given with DFMO", Exp. Cell Res. 2000, vol. 261, pp. 293-302.

(Continued)

*Primary Examiner* — Shailendra Kumar
(74) *Attorney, Agent, or Firm* — Timothy H. Van Dyke; Beusse, Wolter, Sanks & Maire, PLLC

(57) ABSTRACT

Disclosed herein are di-substituted aryl polyamine compounds and methods of making and using the same. The di-substituted polyamine compounds act as PTS targeting agents, which selectively target the polyamine transport system (PTS) with high efficacy and have improved stability in the presence of amine oxidases.

17 Claims, 7 Drawing Sheets

(56) References Cited

OTHER PUBLICATIONS

Burns, M. et al., "Lipophilic lysine-spermine conjugates are potent polyamine transport inhibitors for use in combination with a polyamine biosynthesis inhibitor", J. Med. Chem., 2009, vol. 52, pp. 1983-1993.
Gardner, R. A. et al., "Total synthesis of petrobactin and its homologues as potential growth stimuli for Marinobacter hydrocarbonclasticus, an oil-degrading bacteria", J. Org. Chem., 2004, vol. 69, pp. 3530-3537.
Azmi, A. et al., "Chemoprevention of pancreatic cancer: Characterization of Par-4 and its modulation by 3,3' diindolylmethane (DIM)", Pharm. Res., 2008, vol. 25, pp. 2117-2124.
Kaur, N. et al. "A comparison of chloroambucil- and xylene-containing polyamines leads to improved ligands for accessing the polyamine transport system", J. Med. Chem., 2008, vol. 51, pp. 1393-1401.
Phanstiel, O et al, "Structure-activity Investigations of Polyamineanthracene Conjugates and their Uptake via the Polyamine Transporter", Amino Acids, 2007, vol. 33, No. 2, pp. 305-313.
PubChem Compound, CID 24807068, Jun. 9, 2008.
PubChem Compound, CID 24807458, Jun. 9, 2008.
PubChem Compound, CID 24807066, Jun. 9, 2008.
PCT/US2013/031166, Search Report and Written Opinion, Jul. 2013.
Liao, C et al., "Polyamine transport as a target for treatment of Pneumocystis pneumonia", Antimicrobial Agents and Chemotherapy, 2009, vol. 53, No. 12, pp. 5259-5264.
Cullis, P. M.et al., "Probing the mechanism of transport and compartmentalization of polyamines in mammalian cells", Chem. Biol. ,1999, vol. 6, pp. 717-729.
Seiler, N. et al., "Polyamine transport in mammalian cells. An update", Int. J. Biochem, 1996, vol. 28, pp. 843-861.
Seiler, N. et al., "Polyamine transport in mammalian cells", Int. J. Biochem, 1990, vol. 22, pp. 211-218.
Casero, R. A. M., et al., "Targeting polyamine metabolism and function in cancer and other hyperproliferative diseases", Nat. Rev. Drug Discov., 2007, vol. 6, pp. 373-390.
Phanstiel, O. et al., "The effect of polyamine homologation on the transport and cytotoxicity properties of polyamine—(DNA intercalator) conjugates", J. Org. Chem., 2000, vol. 65, pp. 5590-5599.
Wang, L. et al., "Influence of polyamine architecture on the transport and topoisomerase II inhibitory properties of polyamine DNA-intercalator conjugates", J. Med. Chem., 2001, vol. 44, pp. 3682-3691.
Wang, C.et al., "Synthesis and biological evaluation of N1-(anthracen-9-ylmethyl) triamines as molecular recognition elements for the polyamine transporter", J. Med. Chem., 2003, vol. 46, pp. 2663-2671.
Wang, C.et al., "Molecular requirements for targeting the polyamine transport system: Synthesis and biological evaluation of polyamine anthracene conjugates", J. Med. Chem., 2003, vol. 46, pp. 2672-2682.
Wang, C.et al., "Defining the molecular requirements for the selective delivery of polyamine conjugates into cells containing active polyamine transporters", J. Med. Chem., 2003, vol. 46, pp. 5129-5138.
Kaur, N. et al., "Synthesis and biological evaluation of dihydromotuporamine derivatives in cells containing active polyamine transporters", Journal of Medicinal Chemistry, 2005, vol. 48, pp. 3832-3839.
Gardner, R. A. et al., "N1-Substituent effects in the selective delivery of polyamine-conjugates into cells containing active polyamine transporters", J. Med. Chem., 2004, vol. 47, pp. 6055-6069.
Palmer, Andrew J. et al., "The polyamine transport system as a target for anticancer drug development", Amino Acids, 2010, vol. 38, pp. 415-422.
Soulet, D. et al., "A fluorescent probe of polyamine transport accumulates into intracellular acidic vesicles via a two-step mechanism", J. Biol. Chem., 2004, vol. 279, pp. 49355-49366.
Soulet, D. et al., "Role of endocytosis in the internalization of spermidine-C(2)-BODIPY, a highly fluorescent probe of polyamine transport", Biochem. J., 2002, vol. 367, pp. 347-357.
Belting, M. et al., "Proteoglycan involvement in polyamine uptake", Biochem. J., 1999, vol. 338, pp. 317-323.
Belting, M. et al., "Glypican-1 is a vehicle for polyamine uptake in mammalian cells: A pivotal role for nirosothiol-derived nitric oxide", J. Biol. Chem., 2003,vol. 278, pp. 47181-47189.
Delcros, J. et al., "Effect of spermine conjugation on the cytotoxicity and cellular transport of acridine", J. Med. Chem. 2002, vol. 45, pp. 5098-5111.
Heaton, M. et al., "Methylglyoxal-bis(guanylhydrazone)-Resistant Chinese Hamster Ovary Cells: Genetic Evidence That More Than a Single Locus Controls Uptake", J. Cell. Physiol., 1988, vol. 136, pp. 133-139.
Mandel, J. et al., "Isolation of mutant mammalian cells altered in polyamine transport", J. Cell. Physiol., 1978, vol. 97, pp. 335-344.
Bergeron, R. et al, "The role of charge in polyamine analogue recognition", J. Med. Chem., 1995, vol. 38, pp. 2278-2285.
Phanstiel, O. et al., "Structure-activity investigations of polyamineanthracene conjugates and their uptake via the polyamine transporter", Amino Acids, 2007, vol. 33, pp. 305-313.
Bergeron, R. et al., "A comparison of structure-activity relationships between spermidine and spermine analogue antineoplastics", J. Med. Chem., 1997, vol. 40, pp. 1475-1494.
Kramer, D. et al., "Regulation of polyamine transport by polyamines and polyamine analogues", J. Cell. Physiol., 1993, vol. 155, pp. 399-407.
Byers, T. et al., "Expression of a human gene for polyamine transport in chinese hamster ovary cells", Biochem. J., 1989, vol. 263, pp. 745-752.
Kaur, N. et al., "A comparison of chloroambucil- and xylene-containing polyamines leads to improved ligands for accessing the polyamine transport system", J. Med. Chem., 2008, vol. 51, pp. 1393-1401.
Gahl, W. et al., "Reversal by aminoguanidine of the inhibition of proliferation of human fibroblasts by spermidine and spermine", Chem.-Biol. Interact., 1978, vol. 22, pp. 91-98.
Morgan, D., "Polyamine oxidases and oxidized polyamines", in Physiology of Polyamines, Bachrach, U.; Heimer, Y. M., Eds. CRC Press: Boca Raton, FL, 1989; vol. 1, pp. 203-229.
Flescher, E. et al., "Increased polyamines may downregulate interleukin 2 production in rheumatoid arthritis", J. Clin. Invest., 1989, vol. 83, pp. 1356-1362.
Flescher, E. et al., "Polyamine oxidation down-regulates IL-2 production by human peripheral blood mononuclear cells", J. Immunol., 1989, vol. 142, pp. 907-912.
Flescher, E. et al., "Polyamine-dependent production of lymphocytotoxic levels of ammonia by human peripheral blood monocytes", Immunol. Lett., 1991, vol. 28, pp. 85-90.
Suzuki, O. et al, "Determination of polyamine oxidase activities in human tissues", Experientia, 1984, vol. 40, pp. 838-839.
Seiler, N. et al, "Spermine cytotoxicity to human colon carcinomaderived cells (CaCo-2)", Cell Biol. Toxicol., 2000, vol. 16, pp. 117-130.
Kaur, N. et al., "Designing the polyamine pharmacophore: Influence of N-substituents on the transport behavior of polyamine conjugates", J. Med. Chem., 2008, vol. 51, pp. 2551-2560.
Casero, R. et al., "High specific induction of spermidine/spermine N1-acetyltransferase in a human large cell lung carcinoma", Biochem. J., 1990, vol. 270, pp. 615-620.
Fogel-Petrovic, M.et al., "Structural basis for differential induction of spermidine/spermine N1-Acetyltransferase activity by novel spermine analogs", Mol. Pharmacol., 1997, vol. 52, pp. 69-74.
Coleman, C. et al., "Polyamine analogues inhibit the ubiquitination of spermidine/spermine N1-acetyltransferase and prevent its targeting to the proteasome for degradation", Biochem. J., 2001, vol. 358, pp. 137-145.
Kramer, D. et al., "Effects of novel spermine analogues on cell cycle progression and apoptosis in MALME-3M human melanoma cells", Cancer Res., 1997, vol. 57, pp. 5521-5527.
Barreiro, E. J.et al., "The methylation effect in medicinal chemistry", Chem. Rev., 2011, vol. 111, pp. 5215-5246.

(56) References Cited

OTHER PUBLICATIONS

Kruczynski, A. et al., "Preclinical activity of F14512, designed to target tumors expressing an active polyamine transport system", Invest. New Drugs, 2011, vol. 29, pp. 9-21.

Asaki, T. et al., "Structure-activity studies on diphenylpyrazine derivatives: A novel class of prostacyclin receptor agonists", Bioorg. Med. Chem. Lett., 2007, vol. 15, pp. 6692-6704.

Kane, B. E.; et al., "Synthesis and evaluation of xanomeline analogs-Probing the wash-resistant phenomenom at the M1 muscarinic acetylcholine receptor", Bioorg. Med. Chem. Lett., 2008, vol. 16, pp. 1376-1392.

Middleton, R. et al., "New fluorescent adenosine A1-receptor agonists that allow quantification of ligand-receptor interactions in microdomains of single living cells", J. Med. Chem., 2007, vol. 50, pp. 782-793.

Prugh, J. et al., "A simple method of protecting a secondary amine with tert butyloxycarbonyl (BOC) in the presence of a primary amine", Synthetic Commun., 1992, vol. 22, pp. 2357-2360.

Laduron, F. et al., "Efficient and scalable method for the selective alkylation and acylation of secondary amines in the presence of primary amines", Org. Process Res. Dev., 2005, vol. 9, pp. 102-104.

Fogel-Petrovic, M. et al, "Polyamine and polyamine analog regulation of spermidinelspermine N1-acetyltransferase in MALME-3M human melanoma cells", J. Biol. Chem., 1993, vol. 268, pp. 19118-19125.

Kramer, D. L. et al, "Polyamine analogue induction of the p53-p21WAF1/CIP1-Rb pathway and G1 arrest in human melanoma cells", Cancer Res. 1999, vol. 59, pp. 1278-1286.

Mosmann, T., "Rapid colorimetric assay for cellular growth and survival: Application to proliferation and cytotoxic assays", J. Immunol. Methods, 1983, vol. 65, pp. 55-63.

Kaur, N. et al., "Synthesis and biological evaluation of dihydromotuporamine derivatives in cells containing active polyamine transporters", J. Med. Chem., 2005, vol. 48, pp. 3832-3839.

Gerner, E. et al., "Rationale for, and design of, a clinical trial targeting polyamine metabolism for colon cancer chemoprevention", Amino Acids, 2007, vol. 33, pp. 189-195.

Chen, Y. et al, "Combination therapy with 2-difluoromethylornithine and a polyamine transport inhibitor against murine squamous cell carcinoma", Int. J. Cancer, 2006, vol. 118, pp. 2344-2349.

\* cited by examiner

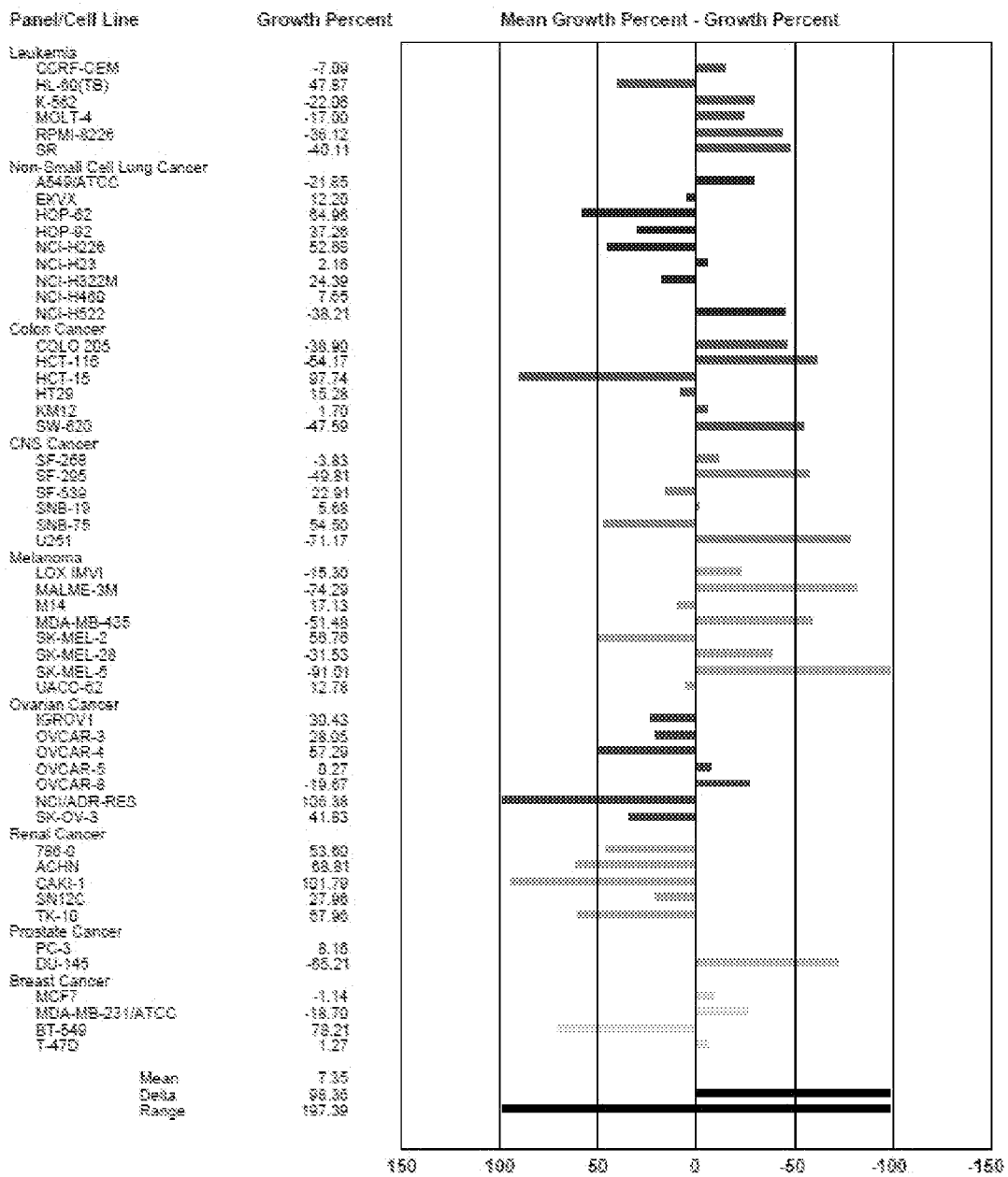
FIG. 1: National Cancer Institute (NCI) 60 cell-line screen of 6a (44Ant44)

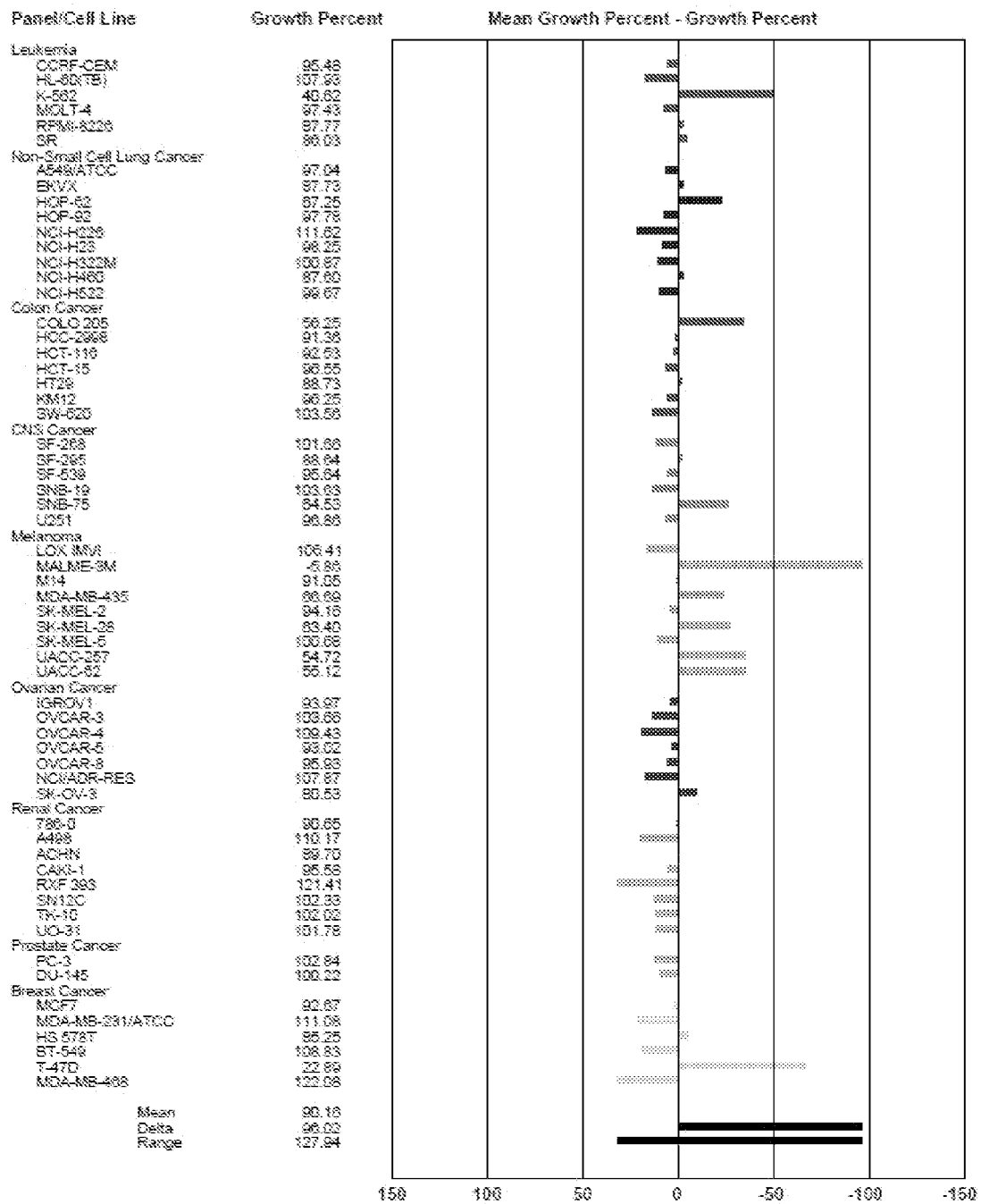
FIG. 2A: NCI 60 cell-line screen of 6b (MeN44Ant44NMe)

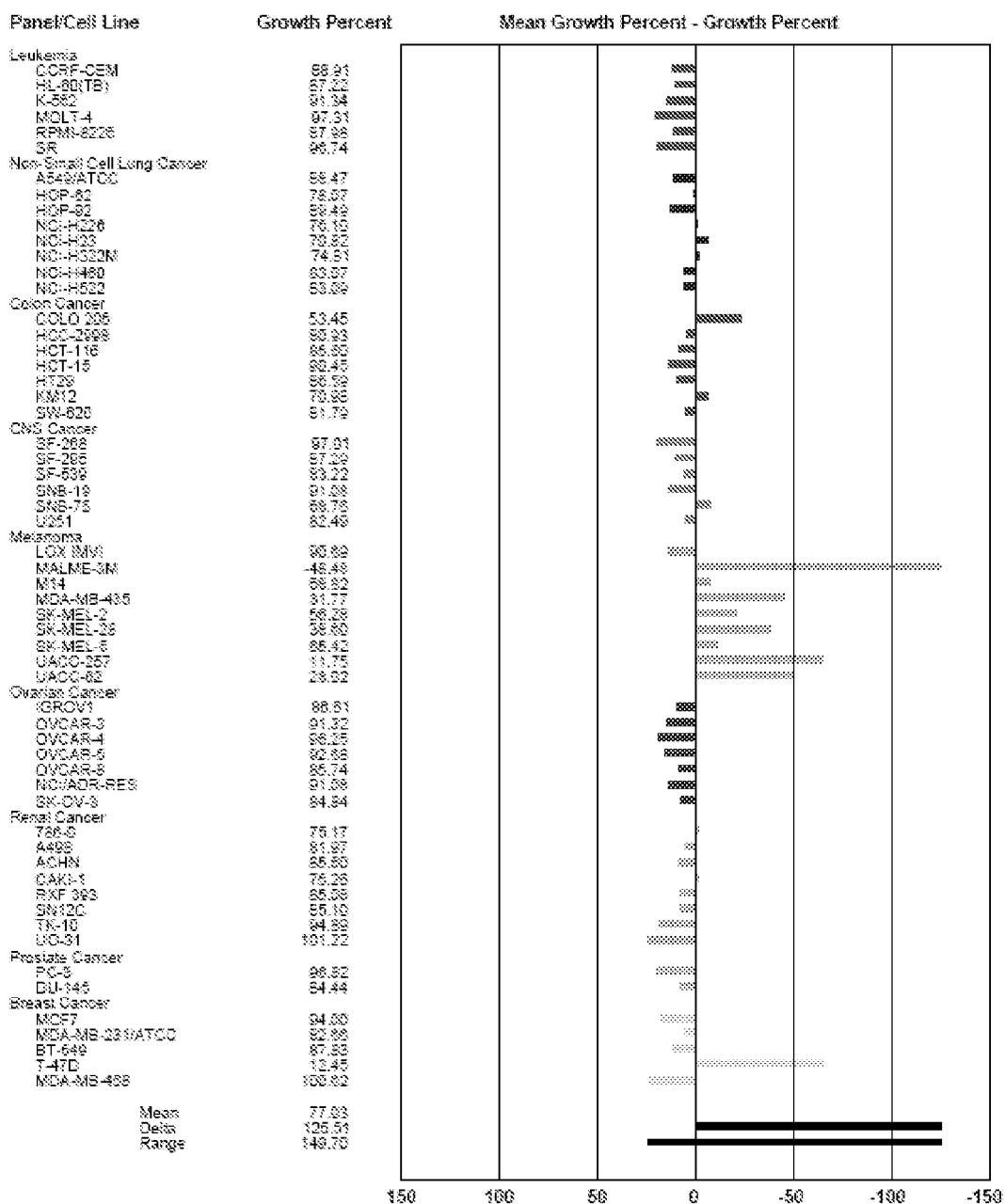
FIG. 2B: NCI 60 cell-line screen of 7b (MeN44Nap44NMe)

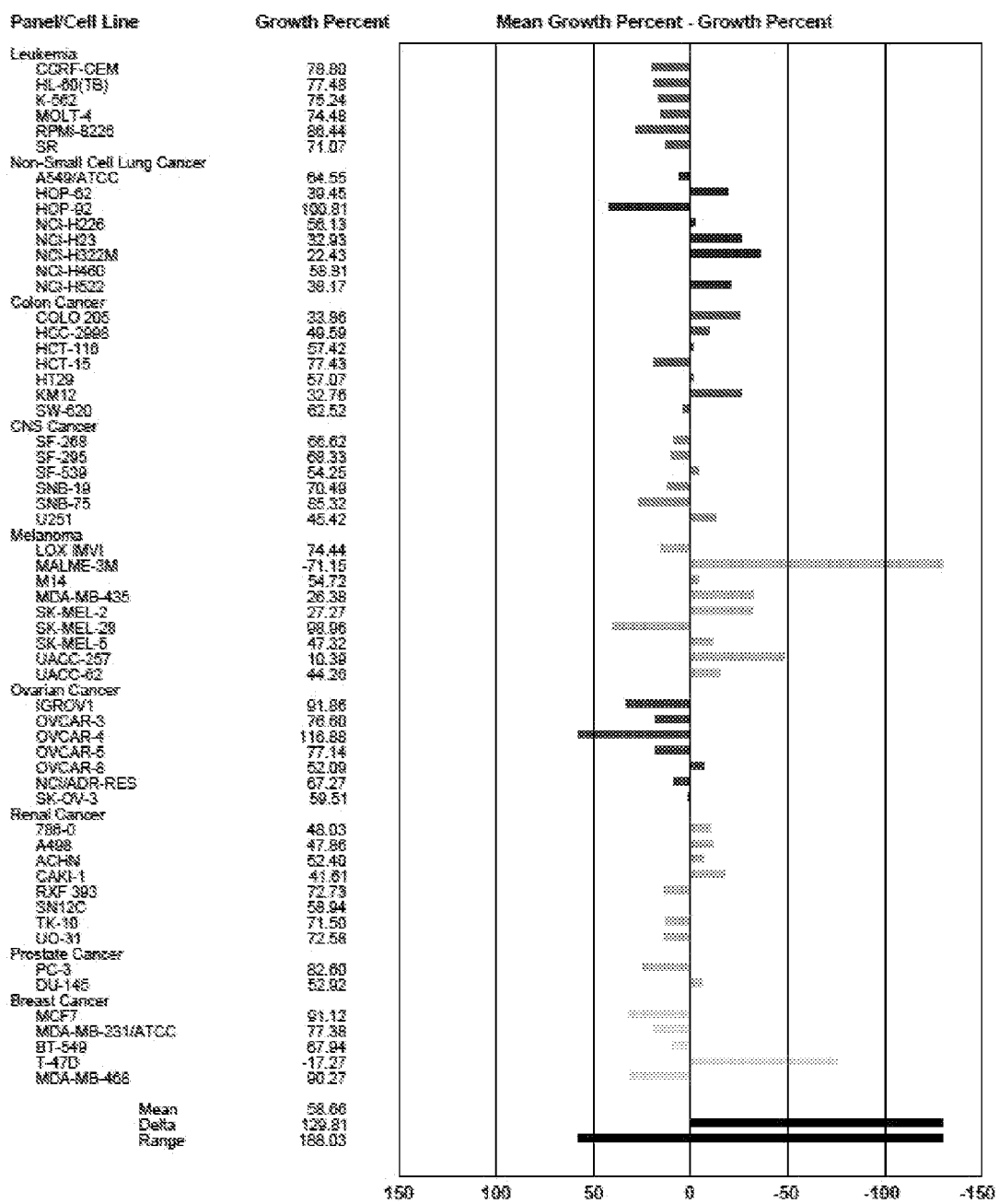
FIG. 2C: NCI 60 cell-line screen of 8b (MeN44Bn44NMe)

POLYAMINE TRANSPORT SELECTIVE THERAPEUTIC AGENTS WITH ENHANCED STABILITY

CROSS-REFERENCE TO RELATED APPLICATIONS

This application is a 371 of PCT/US13/31166, filed Mar. 14, 2013, which claims priority to U.S. Provisional Application No. 61/616,944, filed 28 Mar. 2012, the entirety of which is hereby incorporated by reference.

FIELD OF THE INVENTION

The present invention relates to compositions and methods for the treatment of disorders characterized by unrestrained cell proliferation and/or differentiation, and more particularly to novel polyamine transport ligands, compositions, and methods for their use.

BACKGROUND

Polyamines are essential growth factors for cells.[1] Tumor cells have been shown to contain elevated polyamine levels and have active polyamine transport systems to import exogenous polyamines.[1a] This unique characteristic of cancer cells allows for cell selective drug delivery of polyamine-drug conjugates to particular cell types.[1-2] The polyamine transport system (PTS) is an important target as many cancer cells need to import polyamines in order to sustain their growth rate, especially in the presence of polyamine biosynthesis inhibitors like difluoromethylornithine (DFMO).[1-2] DFMO resembles the natural substrate ornithine for ornithine decarboxylase (ODC), a key enzyme in putrescine biosynthesis.[1-2]

Although the PTS has been recognized as an important target for cell selective drug delivery, the PTS is still poorly understood. What is known is that the PTS is an energy-requiring and carrier mediated process.[3] Recently, in mammalian polyamine transport two models of polyamine transport that have been proposed by Poulin[4] and Belting[5], respectively. Poulin suggested that polyamines enter the cell through an active plasma membrane transporter, followed by the sequestration into polyamine sequestering vesicles (PSV's).[4a] In order for polyamines to internalize within these PSV's, the process needs to be driven by a vesicular H+/polyamine carrier, which also aids in the escape from the PSV.[4a] It was also found that the PSV's colocalized with acidic vesicles of the late endocytic compartment and the trans Golgi.[4a] Belting, on the other hand, provided a multi-step endocytic process where polyamines bind to heparan sulfate proteoglycans in caveolae.[5b] Once the polyamines have bound to heparan sulfate, they are then endocytosed and their heparan sulfate chains are cleaved and further processing by NO liberates the polyamines.[5b]

Drug conjugates, which join a cytotoxic agent to a polyamine, have exhibited selective and enhanced cytotoxicity to cancer cells compared to their normal cell counterparts.[1-2] To assess whether there was any advantage in tethering a polyamine message to a toxic agent, a method was needed to investigate if these drug conjugates were indeed targeting the polyamine transport system. Delcros et. al. demonstrated that the Chinese hamster ovary (CHO) cell line was very effective for identifying drug conjugates which are PTS selective.[6] This cell line was chosen along with its mutant (CHO-MG) in order to demonstrate which drug conjugates effectively utilize the PTS and which ones provide non-specific toxicity.[2g,6] The CHO-MG cell line developed by Flintoff et. al.[7] is polyamine transport deficient. This mutant cell line was developed by treating the CHO cell line with ethyl methanesulfonate and subsequent dosing of the surviving cells with methylglyoxal-bis(guanylhydrazone) (MGBG) to determine their resistance to cytotoxic MGBG.[7b] The surviving cells that were found to be resistant to MGBG were also found to have a marked decrease (less than 1% as compared to the wild type) in the uptake of radiolabeled spermidine, demonstrating a defective PTS.[7b] When evaluating the polyamine drug conjugates, the $IC_{50}$ is determined for both CHO and CHO-MG, with their ratio (CHO-MG $IC_{50}$/CHO $IC_{50}$) being utilized as an evaluator for the PTS selectivity of the compound. Compounds with high CHO-MG/CHO $IC_{50}$ ratios are considered PTS selective.

Several factors can affect PTS selectivity. For example, polyamine oxidase (PAO) activity severely reduces the PTS selectivity of polyamine based drugs via drug degradation. Since polyamine oxidase targets primary amines, it also metabolizes polyamine based drugs. Since cancers have higher polyamine uptake than normal cells, polyamine-based drugs offer the opportunity to selectively target cancers via their reliance on polyamine uptake. Polyamine drugs which are stable to amine oxidases are thus needed to create anti-cancer agents which selectively target cancers, while having enhanced stability to amine oxidases.

BRIEF DESCRIPTION OF THE DRAWINGS

FIG. 1 shows a National Cancer Institute (NCI) 60 cell-line screen of 6a (44Ant44)

FIGS. 2A-2C show a NCI 60 cell-line screen for 6b (MeN44Ant44NMe), 7b (MeN44Nap44NMe), and 8b (MeN44Bn44NMe).

DETAILED DESCRIPTION OF THE INVENTION

Figure 3:
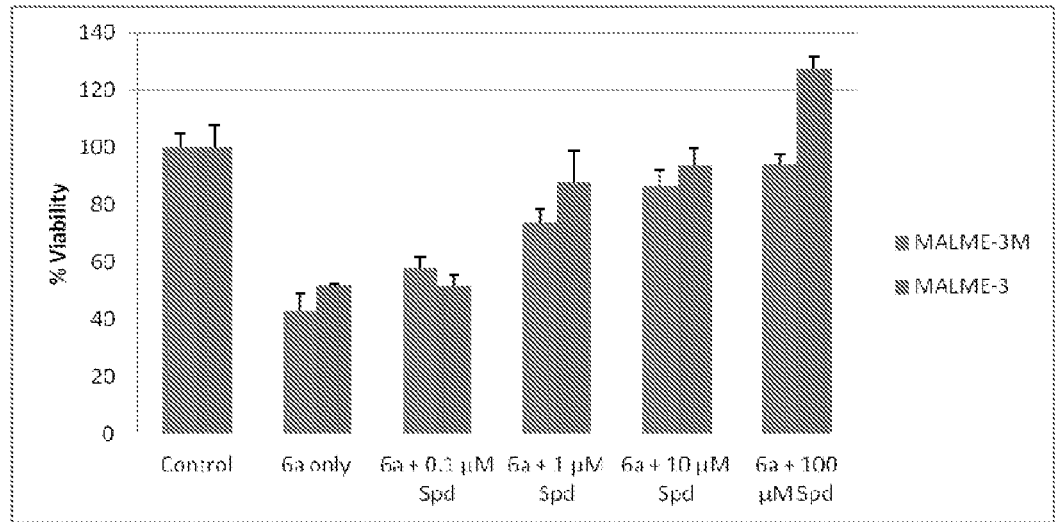
FIG. 3 shows the ability of Spd to rescue MALME-3M and MALME-3 cells treated with compound 6a (44Ant44)[a,b,c,d] [a]Cells were incubated for 96 h at 37° C. with compound 6a at 0.02 μM (MALME-3M) and 0.6 μM (MALME-3). [b]1 mM aminoguanidine (AG, an amine oxidase inhibitor) was determined to be non-toxic and was incubated with cells for 24 h prior to drug addition. [c]Control is no drug control. [d]All experiments were done in triplicate using RPMI 1640 supplemented with 10% FBS and 1% penicillin/streptomycin.

The present inventors have synthesized novel di-substituted aryl polyamine compounds, which selectively target the polyamine transport system (PTS) with high efficacy. Relative to mono-substituted amine based drugs (e.g., those containing a free primary amine as in R—$NH_2$), di-substituted compounds (MeN—R—NMe) better target the PTS. In addition, N-alkylation of the di-substituted compounds also demonstrated improved stability to amine oxidase activity relative to their non-alkylated counterparts. While not wishing to be bound by theory, it is thus believed that the di-substituted N-alkylated compounds described herein may have a longer half-life in vivo and have a lower degree of metabolic degradation. A National Cancer Institute (NCI) screen of 60 human cell lines revealed that the compounds have exquisite selectivity in targeting specific cell types. These included MALME-3M (melanoma), T47D (breast), and K562 (leukemia) cells. Compounds 6b and 7b showed particular specificity to the PTS, as well as enhanced stability to amine oxidase activity.

The present inventors have confirmed the sensitivity of MALME-3M to the compounds described herein, and have shown that the related MALME-3 (normal) cell line is up to 59-fold less sensitive to the drug class, confirming the PTS-targeting specificity. Compound 7b, for example, may be particularly useful for the treatment of melanomas due to its higher selectivity in targeting the cancer line (MALME-3M) over the normal line (MALME-3). Moreover, the large difference in toxicity to the respective cell types (cancer vs. normal) suggests that a reasonable therapeutic window is available for dosing with the compounds described herein in vivo. The compounds described herein could be used alone or in combination with known and/or new therapies (e.g., chemotherapeutic agents or radiation) to treat selected cancers in vivo. In addition, the compounds described herein may be also be suitable as therapies for other cancers, including but not limited to breast cancer and leukemias, based upon the results obtained from the NCI (see FIGS. 1 and 2A-2C).

In accordance with one aspect, there is provided a compound comprising the formula:

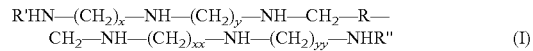

(I)

wherein R is selected from the group consisting of anthracene, naphthalene, and benzene;

wherein R' and R" are independently selected from the group consisting of H and an alkyl group;

wherein x, xx, y, and yy are independently selected from the group consisting of 3 and 4;

or an analog, a conjugate, a derivative, a prodrug, a stereoisomer, or a pharmaceutically acceptable salt thereof.

Aspects of the present invention contemplate all variations of formula (I), and or any analog, a conjugate, a derivative, a prodrug, a stereoisomer, or a pharmaceutically acceptable salt thereof. In one embodiment, R' and R" are independently selected from the group consisting of methyl, ethyl, propyl, isopropyl, and butyl. In a particular embodiment, R' and R"=methyl; x, xx, y, yy are each 4; and R=Ant (anthracene) to define compound 6b. In another particular embodiment, R' and R"=methyl; x, xx, y, yy are each 4; and R=Nap (naphthalene) to define compound 7b.

In another aspect, there is provided a compound comprising the formula:

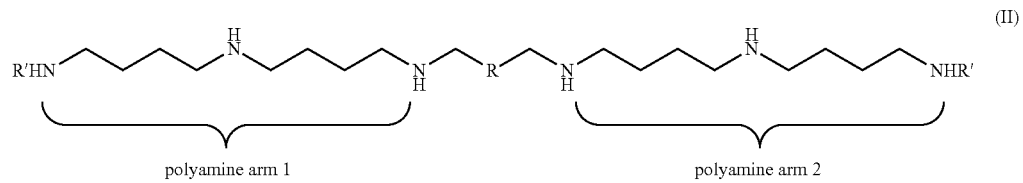

(II)

polyamine arm 1 polyamine arm 2 wherein R is selected from the group consisting of anthracene (Ant), naphthalene Nap), and benzene (Bn); and wherein R' and R" are independently selected from the group consisting of H and an alkyl group;

or an analog, a conjugate, a derivative, a prodrug, a stereoisomer, or a pharmaceutically acceptable salt thereof.

In accordance with another aspect, there is provided a compound comprising the formula:

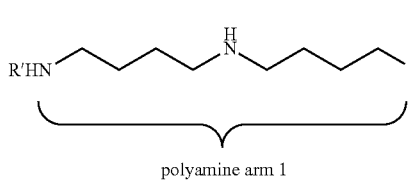 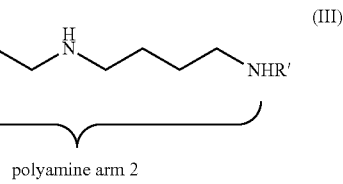

(III)

polyamine arm 1          polyamine arm 2 wherein R is selected from the group consisting of anthracene (Ant) (6b), naphthalene (Nap) (7b), and benzene (Bn) (8b); and wherein R' is methyl;

or an analog, a conjugate, a derivative, a prodrug, a stereoisomer, or a pharmaceutically acceptable salt thereof.

In one embodiment, R=anthracene in formula (III) such that the compound defines compound 6b, or an analog, a conjugate, a derivative, a prodrug, a stereoisomer, or a pharmaceutically acceptable salt thereof.

In another embodiment, R=naphthalene in formula (III) such that the compound defines compound 7b, or an analog, a conjugate, a derivative, a prodrug, a stereoisomer, or a pharmaceutically acceptable salt thereof.

In yet another embodiment, R=benzene in formula (III) such that the compound is compound 8b, or an analog, a conjugate, a derivative, a prodrug, a stereoisomer, or a pharmaceutically acceptable salt thereof.

In accordance with one aspect, there are provided compounds 6b, 7b, 8b, 34a, 34b from the following structures:

(IV)

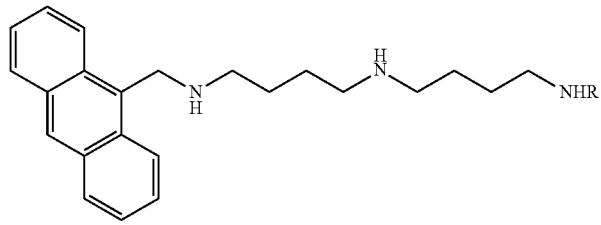

5a: R = H, 3 HCl (Ant44)
5b: R = Me, 3 HCl (Ant44NMe)

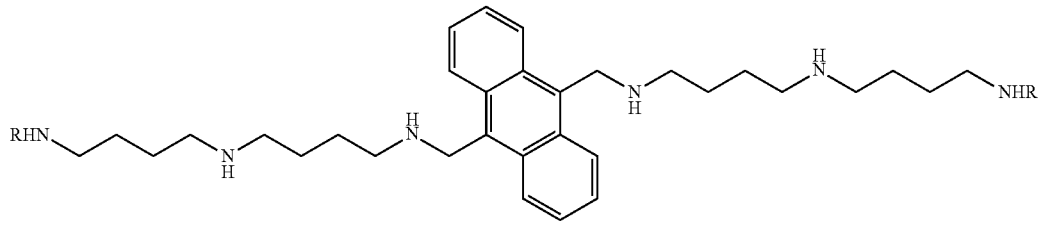

6a: R = H, 6 HCl (44Ant44)
6b: R = Me, 6 HCl (MeN44Ant44NMe)

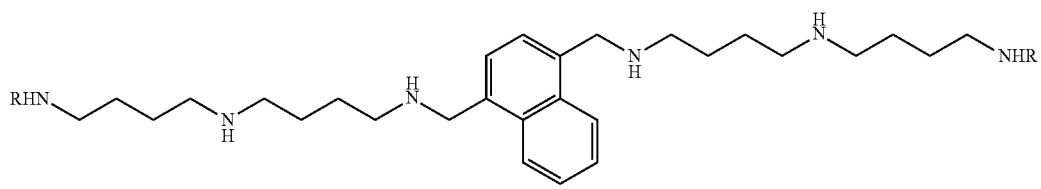

7a: R = H, 6 HCl (44Nap44)
7b: R = Me, 6 HCl (MeN44Nap44NMe)

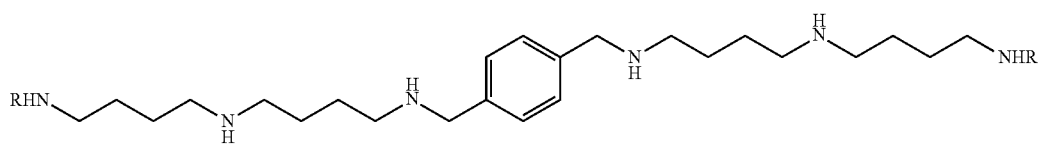

8a: R = H, 6 HCl (44Bn44)
8b: R = Me, 6 HCl (MeN44Bn44NMe)

-continued

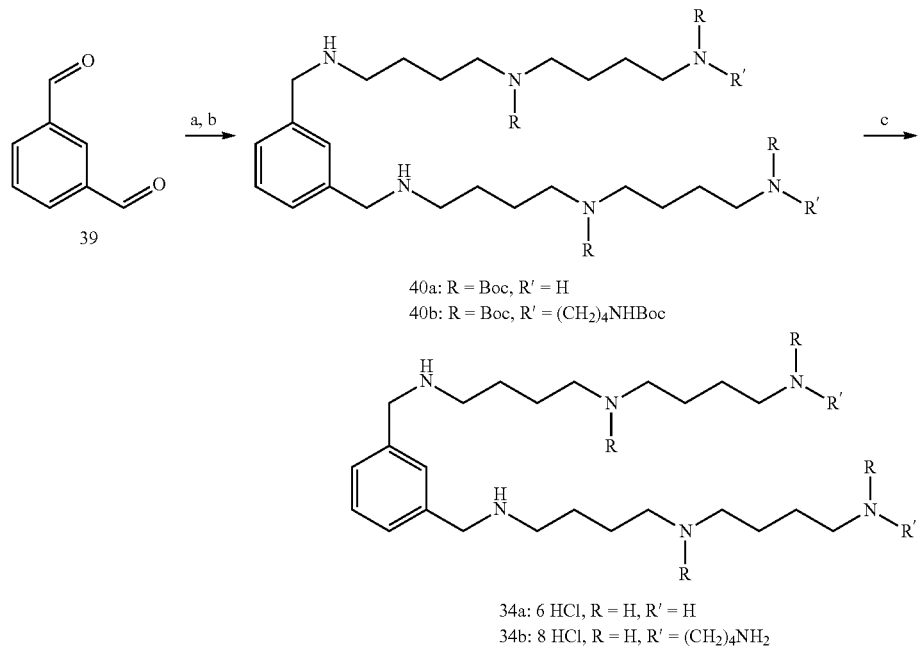

40a: R = Boc, R' = H
40b: R = Boc, R' = (CH$_2$)$_4$NHBoc

34a: 6 HCl, R = H, R' = H
34b: 8 HCl, R = H, R' = (CH$_2$)$_4$NH$_2$ or an analog, a conjugate, a derivative, a prodrug, a stereoisomer, or a pharmaceutically acceptable salt thereof.

In another aspect, there is provided a pharmaceutical composition comprising a compound of formula (I), and a pharmaceutically acceptable carrier.

In another aspect, there is provided a method for preventing or treating a disorder characterized by unrestrained cell proliferation and/or differentiation. The method comprises administering to a subject a composition comprising a compound of formula (I) in an amount effective to reduce an amount of cell proliferation or differentiation. In one embodiment, the disorder is a cancer, such as breast cancer, a leukemia, or a melanoma.

In another aspect, there is provided a method for treating or preventing a melanoma in a subject comprising administering to the subject an effective amount of a compound of formula (I).

In another aspect, there is provided a method for treating or preventing breast cancer in a subject comprising administering to the subject an effective amount of a compound of formula (I).

In another aspect, there is provided a method for treating a cancer in a subject comprising administering to the subject an effective amount of a composition comprising a compound of formula (I) and a chemotherapeutic agent. In one embodiment, the cancer is breast cancer, a leukemia, or a melanoma.

In another aspect, there is provided a method of inhibiting the growth of a cell. The method comprises contacting the cell with an effective amount of a compound of formula (I) such that the cell is targeted via its active polyamine transport system and its growth is inhibited. In one embodiment, the cell is a cancerous cell.

In accordance with yet another aspect of the present invention, there is provided a method for preventing or treating a disorder comprising unrestrained cell proliferation and/or differentiation, wherein the method comprises administering to a subject a composition comprising compound 6b, 7b, 8b, 34a, 34b, combinations thereof, or an analog, a conjugate, a derivative, a prodrug, a stereoisomer, or a pharmaceutically acceptable salt thereof in an amount effective to reduce the number of proliferating cells.

1.1 Definitions

The compounds according to formulas (I)-(V) referred to herein include all compounds encompassed by those formulas and any analog, conjugate, derivative, prodrug, stereoisomer, or pharmaceutically acceptable salt thereof. Formulas (IV) and (V) are understood to encompassed all structures pictured. Thus, by "by compounds of formula (I)," "compounds according to formula (I)," or the like, for example, it is meant the compounds according to formula (I), or any analog, conjugate, derivative, prodrug, stereoisomer, or pharmaceutically acceptable salt thereof. Compounds 34a and 34b also include those compounds, and any analog, conjugate, derivative, prodrug, stereoisomer, or pharmaceutically acceptable salt thereof. The compounds according to formulas (I)-(V), as well as compounds 34a, 34b, may be collectively referred to as "PTS targeting agents" or individually as a "PTS targeting agent."

As used herein, the terms "administering" or "administration" of a compound or agent as described herein to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the terms "alkyl" or "alkyl group" refer to a straight- or branched-chain C1-C10 alkyl group.

As used herein, the term "analog" refers to a compound having a structure similar to that of another one, but differing from it with respect to a certain component. The compound may differ in one or more atoms, functional groups, or substructures, which may be replaced with other atoms, groups, or substructures. In one aspect, such structures possess at least the same or a similar therapeutic efficacy.

The term "cancer" as used herein refers to a class of diseases in which a group of cells display uncontrolled growth, invasion (intrusion on and destruction of adjacent tissues), and sometimes metastasis (spread to other locations in the body via lymph or blood). According to the invention, the cancers to be treated include but not limited to melanomas, leukemias, and breast cancer.

As used herein, the term "cell differentiation" refers to a process by which a less specialized cell develops or matures to possess a more distinct form and function in a subject.

As used herein, the term "cell proliferation" refers to a process increase in cell number by division.

As used herein, the terms "co-administered," "co-administering," or "concurrent administration," when used, for example with respect to administration of a conjunctive agent along with administration of a PTS targeting agent refers to administration of the PTS targeting agent and the conjunctive agent such that both can simultaneously achieve a physiological effect. The two agents, however, need not be administered together. In certain embodiments, administration of one agent can precede administration of the other, however, such co-administering typically results in both agents being simultaneously present in the body (e.g. in the plasma) of the subject.

As used herein, "conjugate" means a compound that has been formed by the joining of two or more compounds by covalent and/or non-covalent bonds.

As used herein, "derivative" refers to a compound derived or obtained from another and containing essential elements of the parent compound. In one aspect, such a derivative possesses at least the same or similar therapeutic efficacy as the parent compound.

As used herein, the terms "disease," "disorder," or "complication" refers to any deviation from a normal state in a subject. In preferred embodiments, the methods and compositions of the present invention are useful in the diagnosis and treatment of diseases characterized at least in part by unrestrained cell proliferation and/or differentiation.

As used herein, by the term "effective amount," "amount effective," "therapeutically effective amount," or the like, it is meant an amount effective at dosages and for periods of time necessary to achieve the desired result.

As used herein, the terms "pharmaceutically acceptable carrier" or "physiologically acceptable carrier" as used herein refer to one or more formulation materials suitable for accomplishing or enhancing the successful delivery of the pharmaceutical composition prepared and delivered according to aspects of the invention.

As used herein, term "pharmaceutically acceptable salt" is intended to include art-recognized pharmaceutically acceptable salts. These non-toxic salts are usually hydrolyzed under physiological conditions, and include organic and inorganic acids and bases. Examples of salts include sodium, potassium, calcium, ammonium, copper, and aluminum as well as primary, secondary, and tertiary amines, basic ion exchange resins, purines, piperazine, and the like. The term is further intended to include esters of lower hydrocarbon groups, such as methyl, ethyl, and propyl.

As used herein, the term "pharmaceutical composition" comprises one or more of the PTS targeting agents described herein as active ingredient(s), or a pharmaceutically acceptable salt(s) thereof, and may also contain a pharmaceutically acceptable carrier and optionally other therapeutic ingredients. The compositions include compositions suitable for oral, rectal, ophthalmic, pulmonary, nasal, dermal, topical, parenteral (including subcutaneous, intramuscular and intravenous) or inhalation administration. The most suitable route in any particular case will depend on the nature and severity of the conditions being treated and the nature of the active ingredient(s). The compositions may be presented in unit dosage form and prepared by any of the methods well-known in the art of pharmacy. Dosage regimes may be adjusted for the purpose to improving the therapeutic response. For example, several divided dosages may be administered daily or the dose may be proportionally reduced over time. A person skilled in the art normally may determine the effective dosage amount and the appropriate regime.

As used herein, the terms "polyamine transport agent," "PTS agents," "PTStargeting agents," "PTS-targeting compounds," or the like includes a compound that selectively utilizes the polyamine transport system (e.g., for cell entry). The PTS targeting agent may be any compound defined by formulas (I)-(V) as set forth herein.

As used herein, the term "preventing" means causing the clinical symptoms of a disorder or disease state not to develop, e.g., inhibiting the onset of disease, in a subject that may be exposed to or predisposed to the disease state, but does not yet experience or display symptoms of the disease state.

As used herein, the term "prodrug" refers to a compound that is converted to a therapeutically active compound after administration, and the term should be interpreted as broadly herein as is generally understood in the art. Generally, but not necessarily, a prodrug is inactive or less active than the therapeutically active compound to which it is converted.

As used herein, the term "stereoisomer" refers to a compound which has the identical chemical constitution, but differs with regard to the arrangement of the atoms or groups in space.

As used herein, term "subject" refers to any animal (e.g., a mammal), including, but not limited to, humans, which may be the recipient of a particular treatment. The term is intended to include living organisms susceptible to conditions or diseases caused or contributed to by unrestrained cell proliferation and/or differentiation where control of polyamine transport is required. The term is intended to include living organisms susceptible to conditions or diseases caused or contributed to by unrestrained cell proliferation and/or differentiation. In one aspect, the disorder includes an elevated usage of the PTS in the subject relative to a normal state. Examples of subjects include humans, dogs, cats, cows, goats, and mice.

As used herein, the terms "treating" or "treatment" refers to both therapeutic treatment and prophylactic or preventative measures, wherein the object is to prevent or slow down (lessen) the targeted pathologic condition or disorder.

1.2 PHARMACEUTICAL COMPOSITIONS

In accordance with one aspect, there are provided pharmaceutical compositions comprising a PTS targeting agent as described herein (e.g., any of the compounds defined by formulas (I)-(V)), or combinations thereof, which can be administered to a patient to achieve a therapeutic effect, e.g., target the polyamine transport activity in the cancer cells of a subject and/or deliver a cytotoxic polyamine-based drug.

In addition to the active ingredients, these pharmaceutical compositions can contain suitable pharmaceutically acceptable carriers comprising excipients and auxiliaries, which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations which can be used orally include push fit capsules made of gelatin, as well as soft, sealed capsules made of gelatin and a coating, such as glycerol or sorbitol. Push fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 150 mM histidine, 0.1% 2% sucrose, and 27% mannitol, at a pH range of 4.5 to 5.5, which is combined with buffer prior to use.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

1.3 DETERMINATION OF A THERAPEUTICALLY EFFECTIVE DOSE

The determination of a therapeutically effective dose is well within the capability of those skilled in the art. A therapeutically effective dose refers to that amount of active ingredient which causes cytotoxicity of cancer cells in a subject and/or metastatic behavior which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred. The data obtained from cell culture assays and animal studies may be used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of container and labeled for treatment of an indicated condition. Such labeling would include amount, frequency, and method of administration.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods described above can be applied to any subject in need of such therapy, including, for example, mammals such as dogs, cats, cows, horses, rabbits, monkeys, and most preferably, humans.

The compositions and methods described herein may be useful for the treatment and/or prevention of any disorder characterized by: (a) unrestrained cell proliferation and/or differentiation; and/or (b) an elevated utilization of the PTS relative to a normal state. In one embodiment, the disorder is an inflammatory bowel disease, e.g., ulcerative colitis.

In another embodiment, the disorder is cancer. In a particular embodiment, the cancer is one of a leukemia, a melanoma, and/or breast cancer. In yet another embodiment, the cancer is a non-small cell lung cancer, colon cancer, CNS cancer, or pancreatic cancer. Indeed, it is expected that any disorder which has active polyamine transport processes should be susceptible to the compounds of this invention which have been optimized to target and utilize the PTS for cell entry. Accordingly, without limitation, the methods and compositions described herein may be utilized for the treatment or prevention of any disorder characterized by unrestrained cell proliferation and/or differentiation where increased utilization of polyamine transport system would bring about a therapeutic effect.

1.4 CONJUGATES

Due to the high selectivity of the PAT-targeting agents described herein for the PAT, aspects of the present invention contemplate the bonding or tying of agents, such as anti-cancer or cytotoxic agents, to the PAT-targeting agent molecule. In this way, the PAT-targeting acts a carrier of the anti-cancer agent to the cell. In one embodiment, a conjugate may be formed between the PAT-targeting agent and a chemotherapeutic agent for the treatment of melanoma or breast cancer. Exemplary chemotherapeutic agents are set forth herein.

1.5 CONJUNCTIVE DELIVERY

In one embodiment, compositions comprising a PTS targeting agent may be administered to the subject alone or along with a conjunctive therapy, such as one or more other additional therapeutic agents, that are active in diseases characterized at least in part by unrestrained cell proliferation and/or differentiation where polyamine transport is involved. In one embodiment, the PTS targeting agent may be delivered along with another chemotherapeutic agent as is known in the art for treating the particular type of cancer. The compositions and methods described herein may be useful for the treatment and/or prevention of any disorder characterized by unrestrained cell proliferation and/or differentiation where polyamine transport is involved. In one embodiment, the disorder is an inflammatory bowel disease, e.g., ulcerative colitis. In another embodiment, the disorder is cancer. In a particular embodiment, the cancer is one of a leukemia, a melanoma, and breast cancer. Thus, compositions comprising a PTS targeting agent may be administered to the patient along with known therapies for treating leukemia, melanoma, and breast cancer in vivo, for example, including chemotherapeutic agents, radiation and/or any other suitable therapy.

By way of example, when the disorder being treated is breast cancer, the conjunctive therapy may comprise radiation, surgery, and/or administration of chemotherapeutic agents, including targeted therapies, such as Abitrexate (Methotrexate), Abraxane (Paclitaxel Albumin-stabilized Nanoparticle Formulation), Adriamycin PFS (Doxorubicin Hydrochloride) Adriamycin RDF (Doxorubicin Hydrochloride), Adrucil (Fluorouracil), Anastrozole, Arimidex (Anastrozole), Aromasin (Exemestane), Capecitabine, Clafen (Cyclophosphamide), Cyclophosphamide, Cytoxan (Cyclophosphamide), Docetaxel, Doxorubicin Hydrochloride Efudex (Fluorouracil), Ellence (Epirubicin Hydrochloride), Epirubicin Hydrochloride, Exemestane, Fareston (Toremifene), Faslodex (Fulvestrant), Femara (Letrozole), Fluorouracil, Folex (Methotrexate), Folex PFS (Methotrexate), Fulvestrant, Gemzar (Gemcitabine Hydrochloride), Ixabepilone, Ixempra (Ixabepilone), Lapatinib Ditosylate Letrozole, Methotrexate, Methotrexate LPF (Methotrexate), Mexate (Methotrexate), Mexate-AQ (Methotrexate), Neosar (Cyclophosphamide), Nolvadex (Tamoxifen Citrate), Novaldex (Tamoxifen Citrate), Paclitaxel, Paclitaxel Albumin-stabilized Nanoparticle Formulation Tamoxifen Citrate, Taxol (Paclitaxel), Taxotere (Docetaxel), Toremifene, Tykerb (Lapatinib Ditosylate), or Xeloda (Capecitabine).

When the disorder being treated is melanoma, the conjunctive therapy may comprise radiation, surgery, and/or administration of chemotherapeutic agents, including targeted therapies, such as imiquimod (Zyclara), Bacille Calmette-Guerin (BCG) vaccine, interleukin-2 immunotherapy with cytokines, Ipilimumab (Yervoy), Vemurafenib (Zelboraf), Dacarbazine (DTIC), and temozolomide (Temodar), a combination uses low doses of interferon, interleukin-2, and temozolomide (Temodar).

The mode of administration for a conjunctive formulation in accordance with the present invention is not particularly limited, provided that the PTS targeting agent and the conjunctive agent are combined upon administration. Such an administration mode may, for example, be (1) an administration of a single formulation obtained by formulating a PTS targeting agent and the conjunctive agent simultaneously; (2) a simultaneous administration via an identical route of the two agents obtained by formulating a PTS targeting agent and a conjunctive agent separately; (3) a sequential and intermittent administration via an identical route of the two agents obtained by formulating a PTS targeting agent and a conjunctive agent separately; (4) a simultaneous administration via different routes of two formulations obtained by formulating a PTS targeting agent and a conjunctive agent separately; and/or (5) a sequential and intermittent administration via different routes of two formulations obtained by formulating a PTS targeting agent and a conjunctive agent separately (for example, a PTS targeting agent followed by a conjunctive agent or its composition, or inverse order) and the like.

The dose of a conjunctive formulation may vary depending on the formulation of the PTS targeting agent and/or the conjunctive agent, the subject's age, body weight, condition, and the dosage form as well as administration mode and duration. One skilled in the art would readily appreciate that the dose may vary depending on various factors as described above, and a less amount may sometimes be sufficient and an excessive amount should sometimes be required.

The conjunctive agent may be employed in any amount within the range causing no problematic side effects. The daily dose of a conjunctive agent is not limited particularly and may vary depending on the severity of the disease, the subject's age, sex, body weight and susceptibility as well as time and interval of the administration and the characteristics, preparation, type and active ingredient of the pharmaceutical formulation. An exemplary daily oral dose per kg body weight in a subject, e.g., a mammal, is about 0.001 to 2000 mg, preferably about 0.01 to 500 mg, more preferably about 0.1 to about 100 mg as medicaments, which is given usually in 1 to 4 portions.

When a PTS targeting agent and a conjunctive agent are administered to a subject, the agents may be administered at the same time, but it is also possible that the conjunctive agent is first administered and then the PTS targeting agent is administered, or that the PTS targeting agent is first administered and then the conjunctive agent is administered. When such an intermittent administration is employed, the time interval may vary depending on the active ingredient administered, the dosage form and the administration mode. For example, when the conjunctive agent is first administered, the PTS targeting agent may be administered within 1 minute to 3 days, preferably 10 minutes to 1 day, more preferably 15 minutes to 1 hour after the administration of the conjunctive agent. When the PTS targeting agent is first administered, for example, then the conjunctive agent may be administered within 1 minute to 1 day, preferably 10 minutes to 6 hours, more preferably 15 minutes to 1 hour after the administration of the PTS-targeting agent.

It is understood that when referring to a PTS targeting agent and a conjunctive agent, it is meant a PTS targeting agent alone, a conjunctive agent alone, as a part of a composition, e.g., composition, which optionally includes one or more pharmaceutical carriers. It is also contemplated that more than one conjunctive agent may be administered to the subject if desired.

In a particular embodiment, the present invention provides for combination therapies, which include the following agents: a polyamine biosynthesis inhibitor (difluoromethylornithine, DFMO) and a PTS targeting agent as described herein. It is known that DFMO increases the potency of polyamine transport-targeting drugs. See Synthesis and Biological Evaluation of $N^1$-(anthracen-9-ylmethyl)triamines as Molecular Recognition Elements for the Polyamine Transporter, Wang, C.; Delcros, J-G.; Biggerstaff, J.; Phanstiel IV, O. *J. Med. Chem.* 2003, 46, 2663-2671. and Structure-activity Investigations of Polyamine-anthracene Conjugates and their Uptake via the Polyamine Transporter. Phanstiel, IV, O.; Kaur, N.; Delcros, J-G. *Amino Acids,* 2007, 33, No. 2, 305-313.). In this regard, a combination therapy involving DFMO and the PTS targeting agents described herein should have increased potency relative to the PTS targeting agent alone.

EXAMPLES

The following example(s) are intended for the purpose of illustration of the present invention. However, the scope of the present invention should be defined as the claims appended hereto, and the following example(s) should not be construed as in any way limiting the scope of the present invention.

1.6 SYNTHESIS

The following paragraphs provide synthesis details for compounds 6b, 7b, and 8b.

Scheme 1.<sup>a</sup> General synthesis of aryl-polyamines (6b, 7b, and 8b):

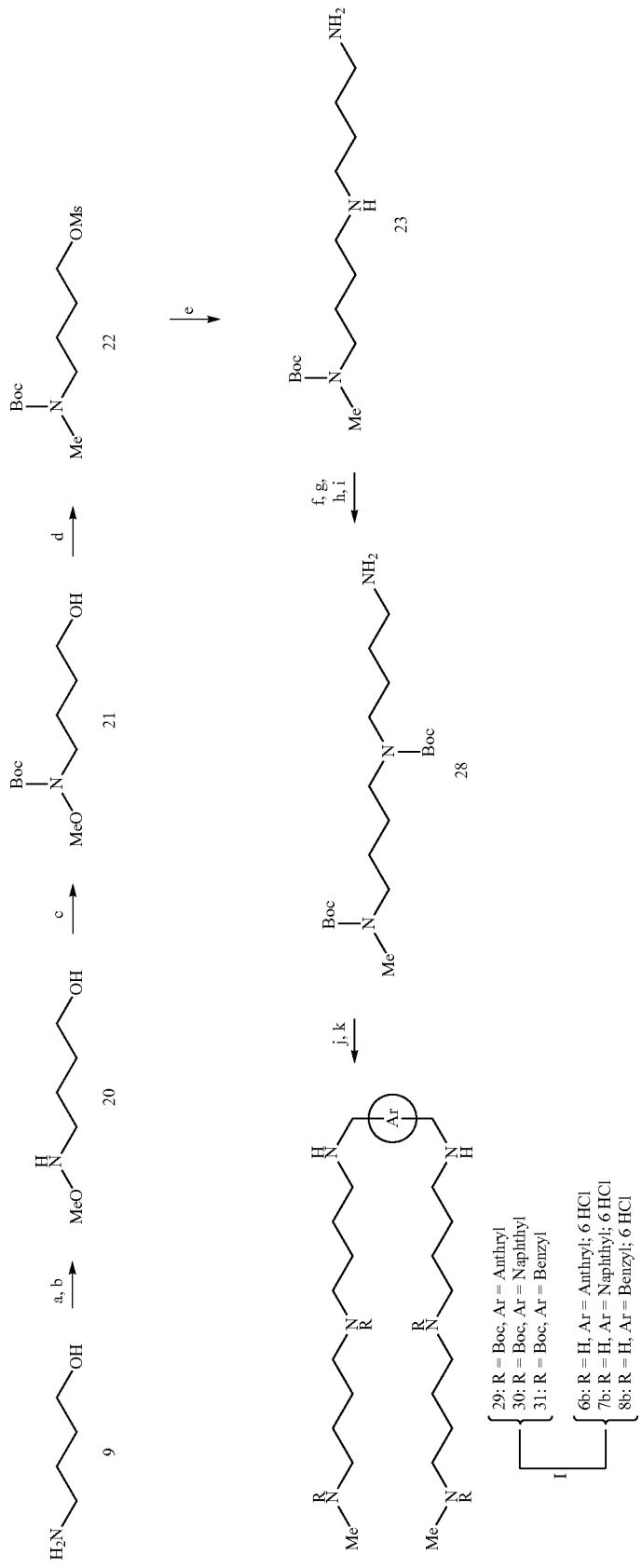

<sup>a</sup>Reagents: (a) Ethyl formate, EtOH; (b) LiAlH₄, THF; (c) 10% TEA/MeOH, di-tert-butyl dicarbonate; (d) MsCl, TEA/CH₂Cl₂; (e) putrescine, K₂CO₃, CH₃CN; (f) salicylaldehyde, Na₂SO₄, 25% MeOH/CH₂Cl₂; (g) di-tert-butyl dicarbonate, MeOH; (h) 0.1M HCl, EtOH; (i) aq. Na₂CO₃, CH₂Cl₂; (j) aryl dialdehyde, 25% MeOH/CH₂Cl₂; (k) NaBH₄, 50% MeOH/CH₂Cl₂; (l) 4M HCl, EtOH The compounds were made in good yield and characterized by $^1$H, $^{13}$C NMR, mass spectrometry and each passed elemental analysis.

1.7 BIOLOGICAL EVALUATION

Once synthesized, the compounds were screened for toxicity in MALME-3M, CHO, and CHO-MG cells. MALME-3M cells were selected due to a NCI-60 cell screen, which showed compound 6b to have incredible selectivity for this cell line. CHO cells were chosen along with a mutant PTS deficient line (CHO-MG*) in order to comment on polyamine transport selectivity.[2c-e, 6] The CHO/CHO-MG* results are shown in Table 1.

The CHO-MG* line was derived from the original CHO-MG line obtained from Flintoff et al.[7] Due to freezer failure, the CHO-MG line had to be re-isolated from a thermally compromised lot. This re-isolation was successful in providing a mutant line, CHO-MG*, with the same phenotype (deficient polyamine transport). However, this cell line proved to be slightly more sensitive to polyamine drugs making the CHO-MG/CHO ratio reduced. For example, CHO-MG/CHO $IC_{50}$ ratio for 5a was 150, whereas the CHO-MG*/CHO $IC_{50}$ ratio for 5a was 43.

1.8 CHO AND CHO-MG* STUDIES

$IC_{50}$ Determinations

CHO cells were chosen along with a mutant cell line (CHO-MG*) to comment on how the synthetic conjugates gain access to the cells.[2c-e, 6] As discussed earlier, the CHO-MG cell line is polyamine-transport deficient and represents a model for alternative modes of entry (other than PTS) including passive diffusion or use of another transporter. The CHO cell line on the other hand, represents cells with high polyamine transport activity.[7, 10c] A comparison of toxicity in these two CHO cell lines allowed for a screen that would detect selective use of the polyamine transporter. This is seen where high utilization of the PTS would be very toxic to CHO cells, however, there would not be the same level of toxicity found in CHO-MG cells.[2c-e, 6] Ultimately, a CHO-MG/CHO $IC_{50}$ can be determined where a high ratio would be achieved for highly PTS selective compounds.

TABLE 1

Biological Evaluation of Polyamine Derivatives (5a-8b) in CHO and CHO-MG* Cells in the Presence and Absence of AG$^{a,b,c,d}$

| Cmpd | CHO-MG* $IC_{50}$ (µM) w/AG | CHO $IC_{50}$ (µM) w/AG | $IC_{50}$ ratio$^c$ w/AG | CHO-MG* $IC_{50}$ (µM) w/o AG | CHO $IC_{50}$ (µM) w/o AG | $IC_{50}$ ratio$^c$ w/o AG |
|---|---|---|---|---|---|---|
| 5a (Ant44) | 13.7 (±1.3) | 0.32 (±0.01) | 42.8 | 2.2 (±0.1) | 1.5 (±0.02) | 1.4 |
| 5b (Ant44NMe) | 10.72 (±1.2) | 2.8 (±0.2) | 3.8 | 11.3 (±2.2) | 2.1 (±0.06) | 5.4 |
| 6a (44Ant44) | >100 | 0.028 (±0.001) | >3571 | 8.4 (±0.7) | 4.0 (±0.3) | 2.1 |
| 6b (MeN44Ant44NMe) | >100 | 0.083 (±0.004) | >1204 | >100 | 0.084 (±0.002) | >1190 |
| 7a (44Nap44) | >100 | 0.022 (±0.002) | >4545 | 52.1 (±7.5) | 5.5 (±0.5) | 9.5 |
| 7b (MeN44Nap44NMe) | >100 | 0.044 (±0.002) | >2272 | >100 | 0.039 (±0.001) | >2564 |
| 8a (44Bn44) | 19.6 (±0.8) | 0.027 (±0.001) | 727 | 56.5 (±3.5) | 10.3 (±0.9) | 5.5 |
| 8b (MeN44Bn44NMe) | 51.5 (±2.6) | 0.030 (±0.001) | 1715 | 54.0 (±2.4) | 0.041 (±0.002) | 1316 |

$^a$Cells were incubated for 48 h at 37° C. with the respective conjugate.
$^b$1 mM AG was incubated with cells for 24 h prior to drug addition
$^c$The ratio denotes the (CHO-MG*/CHO) $IC_{50}$ ratio, a measure of PTS selectivity
$^d$All experiments were done in triplicate As reported earlier,[2g] dramatic differences in CHO and CHO-MG cytotoxicity (Table 1) were observed for 5a, however, the difference was not as great as the original CHO-MG line used (e.g., CHO-MG/CHO $IC_{50}$ ratio of 5a: 148, CHO-MG*/CHO $IC_{50}$ ratio of 5a: 43). This slightly modified CHO-MG* cell line still showed less sensitivity to the polyamine conjugate drugs than CHO, however, not to the extent as the original cell line, CHO-MG. This led to the determination of the $IC_{50}$ values of all drugs previously tested in this modified CHO-MG* cell line.

This CHO screen again showed a dramatic increase in PTS selectivity when a second polyamine message was attached to the opposite side of the cytotoxic (aryl) core (e.g. CHO-MG*/CHO $IC_{50}$ ratio of 6a: >3571, CHO-MG*/CHO $IC_{50}$ ratio of 5a: 43). This was expected as it was thought that an increase in the number of appended polyamine messages would increase the drug conjugates' ability to gain entry via the PTS. As observed earlier[11], however, adding a third polyamine message did not demonstrate the expected increase in PTS selectivity, but instead showed a tremendous decrease in PTS selectivity for the trisubstituted compound 32 (CHO-MG*/CHO $IC_{50}$ ratio of 1).

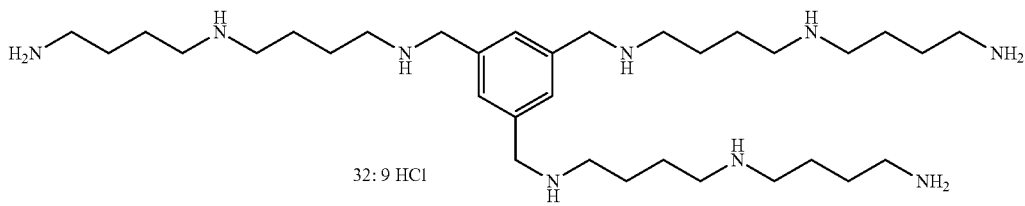

32: 9 HCl

Despite these unprecedented PTS selectivities that were found for the di-substituted polyamine conjugates, they were found to have one distinct limitation. This limitation was found to be their sensitivity to serum amine oxidase Aminoguanidine[13] (AG) is a known inhibitor of serum amine oxidases and is routinely added (1 mM) during our cell culture experiments to avoid polyamine drug degradation by the serum oxidase. Experiments done in the absence of AG showed a severe decrease in the ability of the drugs to exhibit a high level of PTS selectivity (e.g. CHO-MG*/CHO $IC_{50}$ ratio w/AG of 6a: >3571, CHO-MG*/CHO $IC_{50}$ ratio w/o AG of 6a: 2.1). This loss in PTS selectivity in the absence of AG is thought to be attributed to the serum amine oxidases degrading the polyamine conjugates and converting them to other metabolites, which in turn could affect the PTS selectivity of the conjugates.

Prior work demonstrated that N-alkylated polyamines appear to have enhanced metabolic stability through their ability to avoid degradation by serum amine oxidases (polyamine oxidase, PAO).[10a, 13-14] In order to determine if this enhanced metabolic stability could be used to our advantage a series of polyamine conjugate drugs (compounds 5b-8b) were synthesized and tested in CHO and CHO-MG*. The first conjugate synthesized, 5b, showed that metabolic stability could be achieved (CHO-MG*/CHO $IC_{50}$ ratio w/AG=3.8, CHO-MG*/CHO $IC_{50}$ ratio w/o AG=5.4).

Compounds 6b-8b were synthesized to combine the best features of the di-substituted platforms with the N-methylation strategy. In the presence of AG, these compounds exhibited some loss in PTS selectivity, however, still possessed very high PTS selectivities (>2272 to >1204). In the absence of AG, compounds 6b-8b proved that a polyamine based drug conjugate could be designed to be metabolically stable while at the same time being highly PTS selective.

1.9 MALME-3 AND MALME-3M STUDIES. $IC_{50}$ DETERMINATIONS

Once compounds 6a-b, 7a-b, and 8a-8b were evaluated in CHO and CHO-MG*, these compounds were sent to the National Cancer institute (NCI) to conduct its 60 cell-line screen to determine if these compounds could also be potent anti-cancer agents for human cancer cell lines. As shown in FIG. 1, by way of example, this screen showed that 6a was toxic to a wide range of different cancer cells and thus was chosen to advance to the hollow fiber tube assay. While compound 6a was chosen for its general toxicity to numerous cell lines, compound 6b is interesting due to its cell-targeting specificity, especially for the MALME-3M cell line. As shown in FIGS. 2A-2C, dose response curves were generated based upon the 60 cell-line screen at different molar concentrations of each PTS targeting agent 6b, 7b, and 8b.

To generate FIGS. 2A-2C, the respective drug was dosed at 10 µM into each human cancer cell line and cell viability was assessed after a 48 h incubation at 37° C. in an environment of 5% $CO_2$, 95% air and 100% relative humidity. A more descriptive methodology can be found at the NCI website: http://dtp.nci.nih.gov/branches/btb/ivclsp.html. Cell lines which gave bar graphs which extend to the right of the central line were more sensitive to the drug than cell lines which extended to the left of the center line. Cell lines which gave results near the central line indicated that the drug had little effect on the cell line at the 10 µM concentration.

As shown, each of the compounds 6b, 7b, and 8b inhibited the proliferation of melanoma cell lines, particularly the MALME-3M cell line. In addition, to a lesser but still significant extent, each of the compounds 6b, 7b, and 8b exhibited an anti-proliferation effect in breast cancer cell lines, particularly the T-47D cell line.

It was also interesting to note that 6a was seen to enhance the growth of several cell lines, whereas 6b did not show this effect to the same extent. This effect could be explained by the absence of AG during the 60 cell-line screen. As seen previously in CHO cells, cells dosed with polyamine drug in the absence of an amine oxidase inhibitor (aminoguanidine, AG), had dramatic changes in their transport-targeting selectivity due to the action of PAO. Extending this to the NCI screen, we believe that the 6a drug was metabolized to some extent, which modified its toxicity and cell targeting ability. This drug degradation effect, however, was not observed for the N-methylated derivative 6b because in the absence of AG the $IC_{50}$ remained unchanged.

The sensitivity of the MALME-3M cell line to 6b, 7b, and 8b was reconfirmed by NCI through a 5-dose assay where a dose dependent response was observed. Armed with this insight, compounds 5a-8b were evaluated in the MALME-3M (melanoma) cell line and its non-cancerous counterpart MALME-3 obtained originally from the same patient. These matched cell lines provided a method to assess PTS selectivity for the cancer line (MALME-3M) over the non-cancerous cell line (MALME-3). These results can be seen in Table 2.

TABLE 2

Biological Evaluation of Polyamine Derivatives (5-8) in MALME-3M and MALME-3 Cells[a, b, c, d]

| Cmpd | MALME-3 $IC_{50}$ (µM) | MALME-3M $IC_{50}$ (µM) | MALME-3/MALME-3M $IC_{50}$ ratio |
|---|---|---|---|
| 5a (Ant44) | 0.83 (±0.03) | 0.27 (±0.01) | 3.1 |
| 5b (Ant44NMe) | 0.62 (±0.01) | 0.45 (±0.01) | 1.4 |
| 6a (44Ant44) | 0.69 (±0.02) | 0.017 (±0.001) | 41 |
| 6b (MeN44Ant44NMe) | 1.00 (±0.01) | 0.062 (±0.002) | 16 |
| 7a (44Nap44) | 1.27 (±0.09) | 0.018 (±0.001) | 71 |
| 7b (MeN44Nap44NMe) | 0.82 (±0.06) | 0.014 (±0.001) | 59 |

TABLE 2-continued

Biological Evaluation of Polyamine Derivatives (5-8) in MALME-3M and MALME-3 Cells[a, b, c, d]

| Cmpd | MALME-3 IC$_{50}$ (μM) | MALME-3M IC$_{50}$ (μM) | MALME-3/ MALME-3M IC$_{50}$ ratio |
|---|---|---|---|
| 8a (44Bn44) | 0.09 (±0.01) | 0.005 (±0.002) | 18 |
| 8b (MeN44Bn44NMe) | 0.02 (±0.001) | 0.01 (±0.0001) | 2 |

[a]Cells were incubated for 96 h at 37° C. with the respective conjugate.
[b]1 mM AG was determined to be non-toxic and incubated with MALME-3M and MALME-3 cells for 24 h prior to drug addition.
[c]The ratio denotes the (MALME-3/MALME-3M) IC$_{50}$ ratio, a measure of selectivity
[d]All experiments were done in triplicate in RPMI 1640 supplemented with 10% FBS and 1% penicillin/streptomycin.

1.10 IC$_{50}$ DETERMINATIONS IN THE PRESENCE AND ABSENCE OF AG

Prior to the IC$_{50}$ determinations for MALME-3M and MALME-3 in a 96 h assay, IC$_{50}$ values were determined for MALME-3M in a 48 h assay as shown in Table 3 below. In order to further prove the enhanced metabolic stability of methylated compounds 5b, 6b, 7b, and 8b over their non-methylated counter parts (5a, 6a, 7a, and 8a), their IC$_{50}$ values were determined in MALME-3M with and without AG. While the mono-substituted compounds 5a and 5b showed little to no difference in IC$_{50}$ values in the absence of AG, respectively, a dramatic change was seen for the di-substituted compounds (6-8). While the methylated compounds demonstrated the same IC$_{50}$ values in the presence and absence of AG, a profound increase in IC$_{50}$ value (4 to 70 fold) was observed for the non-methylated derivatives. This trend was also observed in CHO (Table 1), where an absence of AG led to increased IC$_{50}$ values for the non-methylated derivatives and not for the N-methylated derivatives. This finding also lends itself well to future in vivo studies as compounds 6b, 7b and 8b can be dosed without the addition of AG.

TABLE 3

Biological Evaluation of Polyamine Derivatives (5-8) in MALME-3M Cells in the Presence and Absence of AG[a, b, c]

| Cmpd | MALME-3M IC$_{50}$ (μM) w/ AG | MALME-3M IC$_{50}$ (μM) w/o AG |
|---|---|---|
| 5a (Ant44) | 0.48 (±0.03) | 0.29 (±0.03) |
| 5b (Ant44NMe) | 0.60 (±0.06) | 0.62 (±0.06) |
| 6a (44Ant44) | 0.088 (±0.004) | 0.29 (±0.005) |
| 6b (MeN44Ant44NMe) | 0.13 (±0.004) | 0.16 (±0.02) |
| 7a (44Nap44) | 0.043 (±0.001) | 0.43 (±0.06) |
| 7b (MeN44Nap44NMe) | 0.10 (±0.002) | 0.17 (±0.006) |
| 8a (44Bn44) | 0.01 (±0.0002) | 0.4 (±0.02) |
| 8b (MeN44Bn44NMe) | 0.007 (±0.0001) | 0.007 (±0.0004) |

[a]Cells were incubated for 48 h at 37° C. with the respective conjugate.
[b]1 mM AG was determined to be non-toxic and incubated with MALME-3M cells for 24 h prior to drug addition.
[c]All experiments were done in triplicate using RPMI 1640 supplemented with 10% Nu-Serum IV and 1% penicillin/streptomycin.

1.11 SPERMIDINE RESCUE EXPERIMENTS

Figure 4:
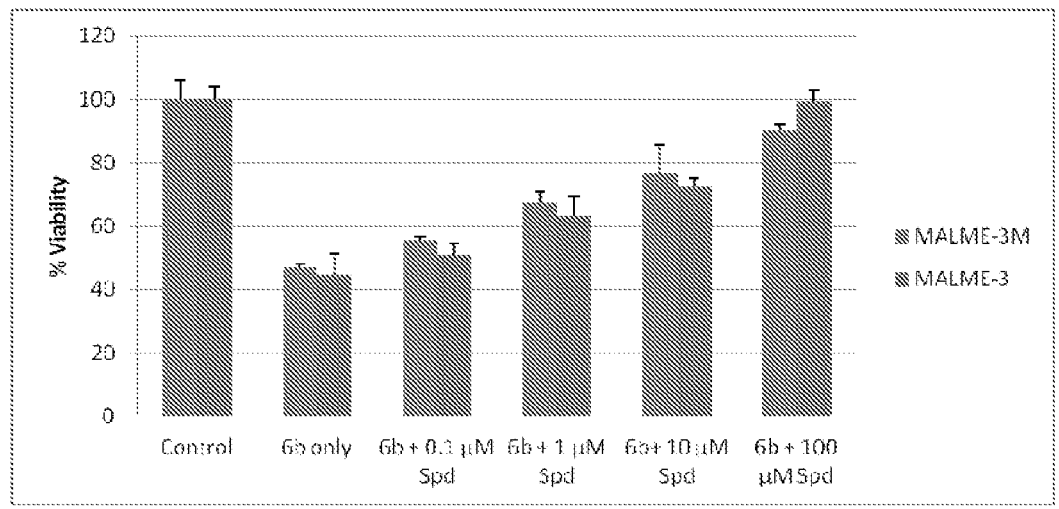
FIG. 4 shows the ability of Spd to rescue MALME-3M and MALME-3 cells treated with compound 6b (MeN44Ant44NMe)[a,b,c,d] [a]Cells were incubated for 96 h at 37° C. with compound 6b at 0.06 μM (MALME-3M) and 1 μM (MALME-3). [b]1 mM AG was determined to be non-toxic and was incubated with cells for 24 h prior to drug addition. [c]Control is no drug control. [d]All experiments were done in triplicate using RPMI 1640 supplemented with 10% FBS and 1% penicillin/streptomycin.
Figure 5:
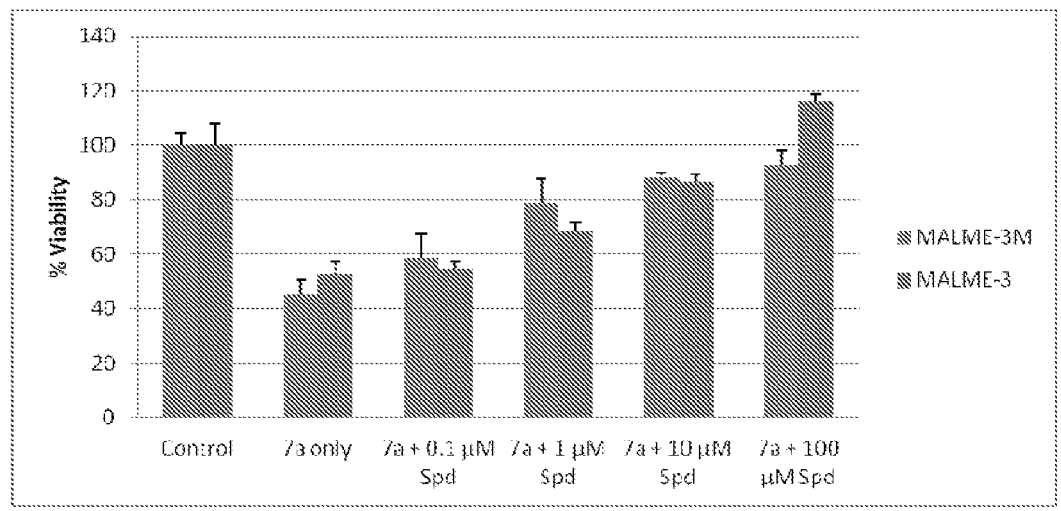
FIG. 5 shows the ability of Spd to rescue MALME-3M and MALME-3 cells treated with compound 7a (44Nap44)[a,b,c,d] [a]Cells were incubated for 96 h at 37° C. with compound 7a at 0.02 μM (MALME-3M) and 1 μM (MALME-3). [b]1 mM AG was determined to be non-toxic and was incubated with cells for 24 h prior to drug addition. [c]Control is no drug control. [d]All experiments were done in triplicate using RPMI 1640 supplemented with 10% FBS and 1% penicillin/streptomycin.
Figure 6:
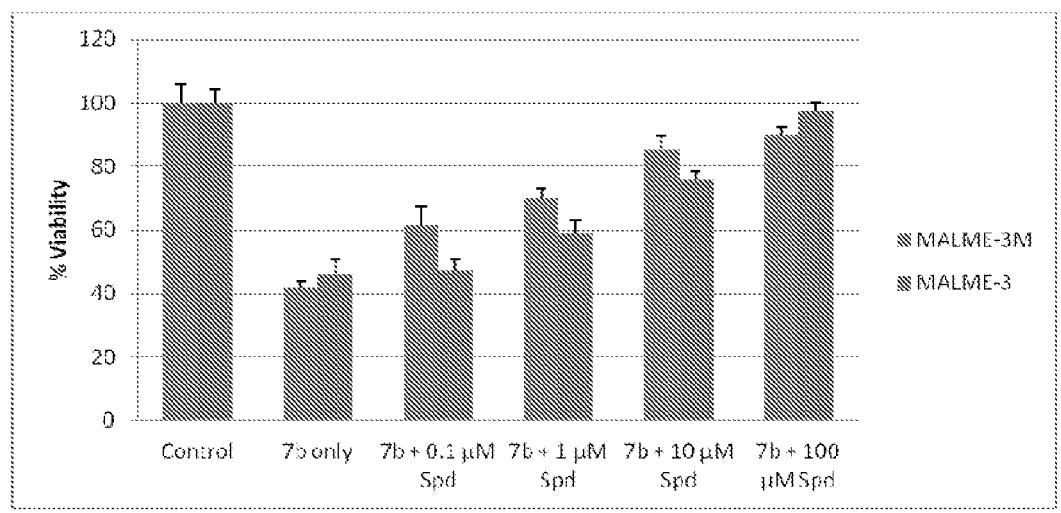
FIG. 6 shows the ability of Spd to rescue MALME-3M and MALME-3 cells treated with compound 7b (MeN44Nap44NMe)[a,b,c,d] [a]Cells were incubated for 96 h at 37° C. with compound 7b at 0.02 μM (MALME-3M) and 0.8 μM (MALME-3). [b]1 mM AG was determined to be non-toxic and was incubated with cells for 24 h prior to drug addition. [c]Control is no drug control. [d]All experiments were done in triplicate using RPMI 1640 supplemented with 10% FBS and 1% penicillin/streptomycin.
Figure 7:
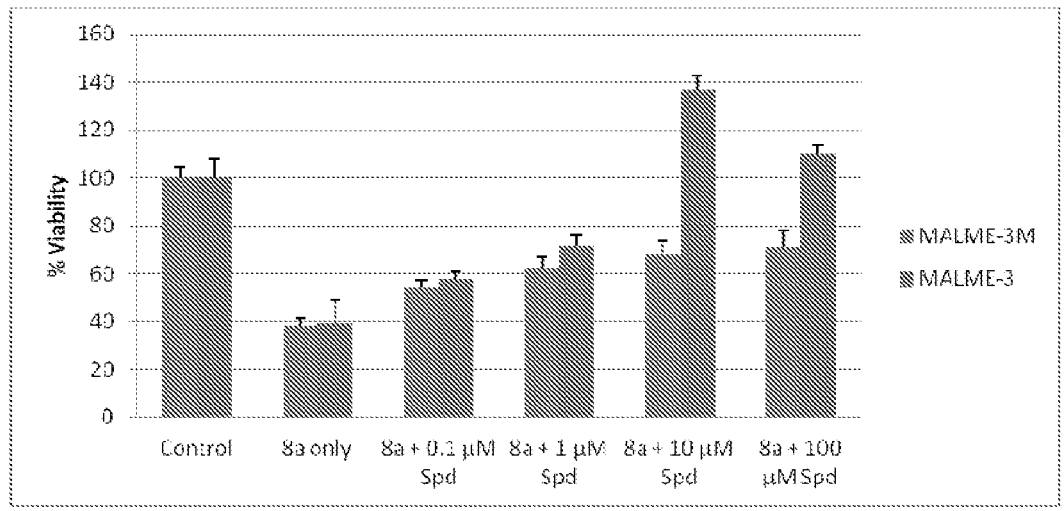
FIG. 7 shows the ability of Spd to rescue MALME-3M and MALME-3 cells treated with 8a (44Bn44)[a,b,c,d] [a]Cells were incubated for 96 h at 37° C. with compound 8a at 0.01 μM (MALME-3M) and 0.1 μM (MALME-3). [b]1 mM AG was determined to be non-toxic and was incubated with cells for 24 h prior to drug addition. [c]Control is no drug control. [d]All experiments were done in triplicate using RPMI 1640 supplemented with 10% FBS and 1% penicillin/streptomycin.
Figure 8:
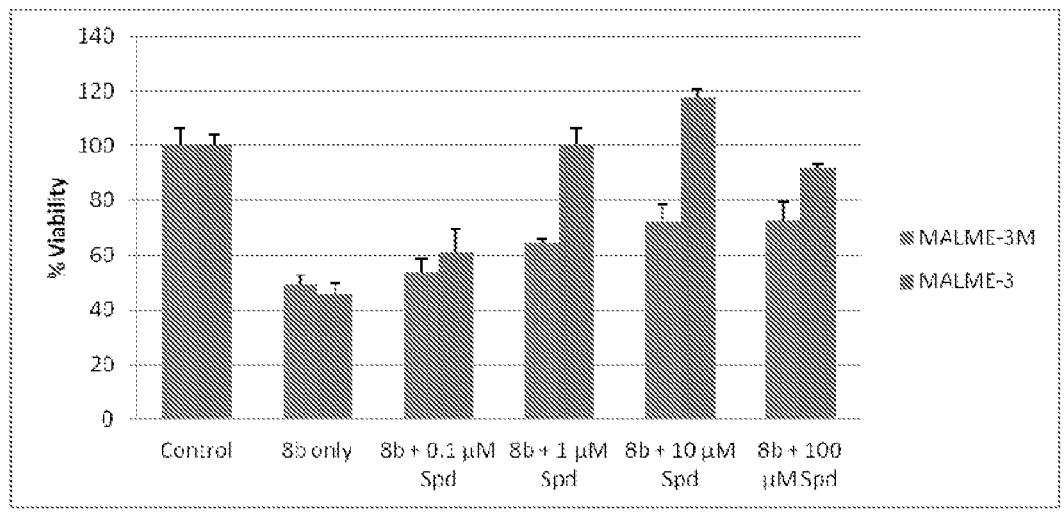
FIG. 8 shows the ability of Spd to rescue MALME-3M and MALME-3 cells treated with 8b (MeN44Bn44NMe)[a,b,c,d] [a]Cells were incubated for 96 h at 37° C. with compound 8b at 0.01 μM (MALME-3M) and 0.02 μM (MALME-3). [b]1 mM AG was determined to be non-toxic and was incubated with cells for 24 h prior to drug addition. [c]Control is no drug control. [d]All experiments were done in triplicate using RPMI 1640 supplemented with 10% FBS and 1% penicillin/streptomycin.

In order to validate that these drugs were toxic due to their use of the polyamine transport system, spermidine rescue experiments were conducted. Spermidine is a native polyamine and uses the PTS for cell entry. High concentrations of spermidine should outcompete the PTS-targeting drugs for cell entry. In this regard, spermidine when dosed at a non-toxic concentration should rescue the cells from the toxic effects of the PTS targeting agents. Spermidine was shown to be non-toxic up to 100 μM in both MALME cell lines. The results are shown in the FIGS. 3-8. Significant rescue was observed with either 100 μM or 10 μM spermidine (i.e., non-toxic dose) for most of the drugs tested at their respective IC$_{50}$ concentrations. Both the anthryl and naphthyl systems when dosed at their IC$_{50}$ concentrations gave >92% viability at 10 μM spermidine validating their use of the PTS. Rescue was observed from the initial 50% viability to >92% viability after co-dosing 10 μM spermidine.

The benzyl system (8b) showed a reduced rescue effect by spermidine (75% viability at 10 μM spermidine) and demonstrated significantly reduced targeting capabilities (8b: MALME-3M/MALME-3 IC$_{50}$ ratio=2, vs 59 for 7b). These two observations suggested that 8b likely enters cells by multiple pathways including a non-PTS uptake pathway. The fact the spermidine at a significantly higher dose was unable to significantly rescue cells from 8b is consistent with this speculation. In contrast, 6b and 7b were deemed very PTS-selective due to the high degree of rescue by exogenous spermidine and their high selectivity in targeting the MALME-3M line over the MALME-3 counterpart (see Table 2).

In summary, compounds 6b and 7b are preferred PTS-targeting drugs due to their enhanced stability to amine oxidase activity, which allows them to be dosed without aminoguanidine as a co-additive. Moreover, these two compounds (6b and 7b) demonstrated significant 16- and 59-fold ability to target cancer cell line (MALME-3M) over the normal MALME-3 line, respectively. Compound 7b, the naphthyl derivative, would be preferred for use in the treatment of a melanoma due to its higher selectivity in targeting the cancer line over the normal line.

As stated above, in an effort to determine if the cytotoxicities seen for compounds 6-8 were polyamine transport related, MALME-3M and MALME-3 were dosed near the IC$_{50}$ value of each drug. These cells were also treated with increasing amounts of spermidine to see if it could outcompete compounds 6-8 for cellular entry and thus rescue the cells. Compounds 6-7 each showed that exogenous spermidine was able to significantly rescue (~90% viability) MALME-3M and MALME-3 cells from the cytotoxicity of these compounds. This supports the premise that these compounds gain access to these cells primarily via the PTS. When exogenous spermidine was added to 8a and 8b (FIGS. 7-8 respectively), a much lower level of rescue was observed in MALME-3M (<80% viability). However, complete rescue was observed in MALME-3. Since the viability of MALME-3M cells could be partially rescued by spermidine, compounds 8a and 8b may gain access via the PTS and via non-PTS related pathway(s). These results correlate well with the finding that 6 and 7 (anthryl and naphthyl cores respectively) prefer MALME-3M and its upregulated PTS over MALME-3. In contrast, 8a and 8b did not demonstrate the same degree of selectivity.

It is also interesting to note that while spermidine was able to rescue both MALME-3M and MALME-3 from the toxic effects of 6-8, a large excess of spermidine was necessary. As seen in FIGS. 3-8, between 10 and 100 μM spermidine was needed to get significant rescue. Since compounds 6-8 exhibited ~50% viability at very low doses (0.01 μM to 0.06 μM for MALME-3M, and 0.02 μM to 1 μM for MALME-3), a very large molar excess of spermidine was necessary to outcompete these compounds. These results can be partially attributed to significant differences in Ki values (lower Ki=better binding affinity) observed in L1210 cells for compounds 6a (Ki=0.39 μM), 7a (Ki=0.17 μM), and 8a (Ki=0.52 μM) as compared to spermidine (Ki=2.46 μM).[3d, 12] These findings suggest that these di-substituted compounds have a much higher affinity for the PTS as compared to spermidine, thus requiring a large molar excess of spermidine to outcompete 6-8 for the PTS.

1.12 ORIENTATION OF THE APPENDED POLYAMINE CHAINS

Di-substituted derivatives 34a and 34b were also generated to determine if the orientation of the appended polyamine chains influenced the ability of the compound class to target the polyamine transport system. These meta-substituted systems (34a and 34b) could then be compared to the para-substituted benzene derivative 8a. As shown in Scheme 2 below, the synthesis began with the reductive amination of aldehyde 39 with the protected polyamine 37a or 37b.[36] Extra caution was taken to dry methanol and NaBH$_4$ so as to minimize the generation of alcohol byproducts, which were difficult to separate from the desired product. This became evident in the purification of 40a, as the mono-alcohol side product and the excess amine used initially had very similar R$_f$ values to the desired product.

The purification problem was alleviated through the use of a unique TLC solvent system (hexanes/NH$_4$OH/freshly distilled THF) which ultimately led to the isolation of compound 40a. Deprotection of 40a gave the final HCl salt 34a. This provided 34a in 24% yield over 3 steps. The related compound 40b was isolated in 55% yield using the more conventional CH$_2$Cl$_2$/MeOH/NH$_4$OH TLC solvent system. Finally, 40b was deprotected to give the di-substituted extended amine system 34b in 98% yield. In sum, 34b was generated in 54% yield over these steps.

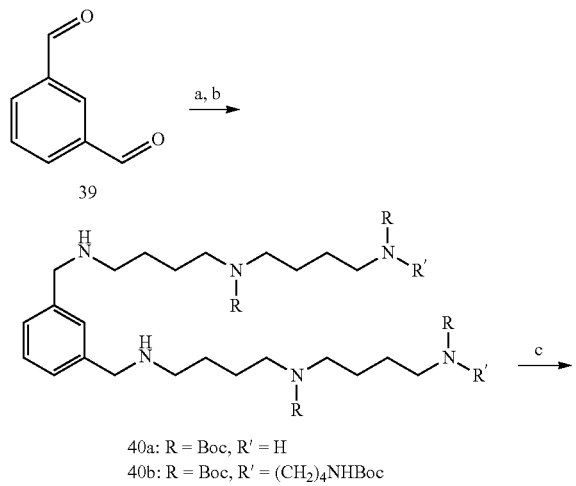

Scheme 2. [a]Synthesis of 34a and 34b

40a: R = Boc, R' = H
40b: R = Boc, R' = (CH$_2$)$_4$NHBoc

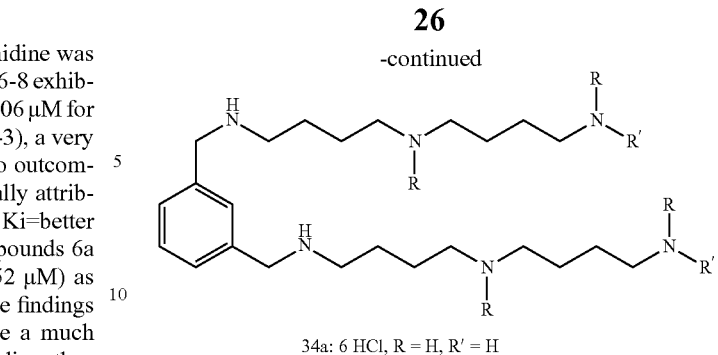

34a: 6 HCl, R = H, R' = H
34b: 8 HCl, R = H, R' = (CH$_2$)$_4$NH$_2$

[a]Reagents: (a) 25% MeOH/CH$_2$Cl$_2$, respective Boc-protected polyamine; (b) 50% MeOH/CH$_2$Cl$_2$, NaBH$_4$; (c) 4M HCl/EtOH

TABLE 4

Biological Evaluation of Polyamine Derivatives (32, 34a, and 34b) in CHO and CHO-MG* Cells[a, b, c, d, e]

| Compound | MTD (μM) in CHO | CHO-MG* IC$_{50}$ (μM) | CHO IC$_{50}$ (μM) | CHO-MG*/CHO IC$_{50}$ (μM) |
|---|---|---|---|---|
| 32 (Trimer44) | 80 | >100 | >100 | ND |
| 34a (mBn44) | 0.01[f] | 30.0 (±0.8) | 0.028 (±0.002) | 1072 |
| 34b (mBn444) | 0.01[g] | 13.4 (±0.8) | 0.04 (±0.007) | 335 |

[a]CHO and CHO-MG* cells were incubated with 1 mM AG for 24 h prior to drug addition.
[b]The ratio denotes the (CHO-MG*/CHO) IC$_{50}$ ratio, a measure of PTS selectivity.
[c]Cells were incubated for 48 h at 37° C. with the respective conjugate.
[d]All experiments were done in triplicate.
[e]ND: not determined due to the low toxicity in both CHO cell lines.
[f]At 0.01 μM, 34a displayed ~90% viability.
[g]At 0.01 μM, 34b displayed ~90% viability.
Note:
MTD = maximum tolerated dose The above compounds were evaluated in the CHO and CHO-MG* screen to determine if the meta substituted compound s were also PTS selective agents. The maximum tolerated dose (MTD) of each agent (Table II-1) was determined along with the CHOMG/CHO IC50 ratio. As discussed earlier, 1,3,5-tri-substituted analogue 32 exhibited a very high IC$_{50}$ value in both CHO and CHO-MG* (>100 μM for both), demonstrating it to be fairly non-toxic. This was in stark contrast to the 1,4-di-substituted platform used for 8a which was very PTS selective (CHO-MG*/CHO IC$_{50}$ ratio: 727). This proved to be a very interesting finding as both 32 and 8a possess near identical K, values in L1210 cells (0.52±0.11 and 0.49±0.02 respectively).[38] This indicated that while these two compounds bind to the cell surface equally as well, a feature is present which imparts significant toxicity with 8a and less so with 32.

To better understand these differences, new derivatives were made to investigate whether the orientation of the polyamine messages is a driver of this phenomenon. The results for 34a and 34b in CHO and CHO-MG* proved to be very interesting. Both compounds were shown to be highly PTS selective as seen in Table 4. Compound 34a was seen to be the most PTS selective (CHO-MG*/CHO IC$_{50}$ ratio: 1072), and clearly demonstrated that the third polyamine arm of 32 eliminated toxicity. For example, in the CHO cell line, 32 is >3500-fold less toxic than 34a. Compound 34b was shown to be less PTS selective (CHO-MG*/CHO IC$_{50}$ ratio: 335) than its counterpart 34a, demonstrating that the longer polyamine message (tetraamine arm) lowered the PTS selectivity of the design. A similar finding was noted in the comparison of mono-substituted triamines and tetraamines.[39]

1.13 EXPERIMENTAL

1.13.1 Materials

Silica gel (32-63 µm) and chemical reagents were purchased from commercial sources and used without further purification. All solvents were distilled prior to use. All reactions were carried out under an $N_2$ atmosphere. $^1H$ and $^{13}C$ spectra were recorded at 400 or 75 MHz, respectively. TLC solvent systems were listed as volume percents, and $NH_4OH$ referred to concentrated aqueous $NH_4OH$. All tested compounds (6-8) provided satisfactory elemental analyses.

1.13.2 Biological Studies

CHO and CHO-MG cells were grown in RPMI 1640 medium supplemented with 10% fetal calf serum and 1% penicillin/streptomycin. Note: the media must contain L-proline (2 µg/mL) for proper growth of the CHO-MG cells. MALME-3M cells were grown in RPMI 1640 medium supplemented with 10% FBS and 1% penicillin/streptomycin. All cells were grown at 37° C. under a humidified 5% $CO_2$ atmosphere Aminoguanidine (1 mM) was added to the growth medium to prevent oxidation of the drugs by the enzyme (bovine serum amine oxidase) present in calf serum. Cells in early to mid-log phase were used.

1.13.3 $IC_{50}$ Determinations

Cell growth was assayed in sterile 96-well microtiter plates (Costar 3599, Corning, N.Y., USA). CHO and CHO-MG* cells were plated at 10,000 cells/mL. MALME-3M and MALME-3 cells were plated at 5,000 cells/mL. Drug solutions (10 µL per well) of appropriate concentration were added after an overnight incubation for each CHO cell line (90 µL). 48 h MALME-3M experiments were conducted using 10% Nu-Serum IV, and 96 h MALME-3M and MALME-3 experiments were conducted using 10% FBS. After exposure to the drug for 48 h (CHO, CHO-MG*, and MALME-3M) or 96 h (MALME-3M and MALME-3), cell growth was determined by measuring formazan formation from 3-(4,5-dimethylthiazol-2-yl)-5-(3-carboxymethoxyphenyl)-2-(4-sulphenyl)-2H-tetrazolium) inner salt (MTS) using a SynergyMx Biotek microplate reader for absorbance (490 nM) measurements.[24]

1.13.4 Synthetic Procedures and Characterization

N1,N1'-(Anthracene-9,10-diylbis(methylene))bis (N4-(4-(methylamino)butyl)butane-1,4-diamine), 6b Orange solid (93%); $^1H$ NMR ($D_2O$) δ 8.33 (dd, 4H), 7.82 (dd, 4H), 5.18 (s, 4H), 3.38 (t, 4H), 3.16 (12H), 2.76 (s, 6H), 1.84 (m, 16H); $^{13}C$ NMR ($D_2O$) δ 185.5, 129.9, 127.7, 125.1, 124.0, 48.2, 47.5, 46.9, 46.8, 42.9, 32.7, 22.9, 22.8, 22.7, 22.6. HRMS (FAB) m/z calc for $C_{34}H_{56}N_6$ (M+H) 549.4566. found 549.4639. Elemental analysis $C_{34}H_{62}N_6Cl_6 \cdot 1.25H_2O$ theory C, 51.69; H, 8.23; N, 10.64. found C, 51.66; H, 8.05; N, 10.49.

N1,N1'-(Naphthalene-1,4-diylbis(methylene))bis (N4-(4-(methylamino)butyl)butane-1,4-diamine), 7b Yellow solid (98%); $^1H$ NMR ($D_2O$) δ 8.25 (dd, 2H), 7.83 (dd, 2H), 7.75 (s, 2H), 4.85 (s, 4H), 3.34 (t, 4H), 3.15 (t, 12H), 2.75 (s, 3H), 1.83 (m, 16H); $^{13}C$ NMR ($D_2O$) δ 134.3, 132.2, 131.5, 130.9, 126.8, 51.2, 51.0, 50.2, 49.9, 35.7, 25.9, 25.8, 25.6. Elemental analysis $C_{30}H_{60}N_6Cl_6 \cdot 2H_2O$ theory C, 47.82; H, 8.56; N, 11.15. found C, 47.85; H, 8.35; N, 10.82

N1,N1'-(1,4-Phenylenebis(methylene))bis(N4-(4-(methylamino)butyl)butane-1,4-diamine), 8b While solid (99%); $^1H$ NMR ($D_2O$) δ 7.61 (s, 4H), 4.28 (s, 4H), 3.21-3.12 (t, 16H), 1.78 (m, 16H); $^{13}C$ NMR ($D_2O$) δ 135.0, 133.4, 53.5, 51.1, 49.7, 49.4, 35.6, 25.7, 25.6, 25.5. HRMS (FAB) m/z calc for $C_{26}H_{52}N_6$ (M+H) 449.4253. found 449.4326. Elemental analysis $C_{26}H_{58}N_6Cl_6$ theory C, 46.79; H, 8.76; N, 12.59. found C, 46.69; H, 8.82; N, 12.33.

4-Methylamino-butan-1-ol, 20.[18]

To a stirred solution of 9 (4.31 g, 48.4 mmol) in EtOH (50 mL) was added ethylformate (5.86 mL, 75.5 mmol) and the mixture was stirred at reflux for 18 hrs under $N_2$. The solution was evaporated under reduced pressure, and the crude product was used for the next step without further purification. The crude reaction mixture was dissolved in THF (25 mL) and added to a suspension of $LiAlH_4$ (5.50 g, 145 mmol) in THF (50 mL) dropwise under a drying tube while stirring. The reaction mixture was brought to reflux and monitored by TLC (20% $EtOH/80\% CHCl_3$) and $^1H$ NMR ($CDCl_3$). After 2 hours, the starting material was consumed, and $H_2O$ (4.16 mL) was added to the cooled reaction mixture, followed by 4 M NaOH (4.16 mL) and $H_2O$ (12.5 mL) while stirring vigorously. The precipitate was then removed by filtration, and the filtrate concentrated in vacuo. The residue was re-dissolved in $CHCl_3$, dried over $Na_2SO_4$, filtered and concentrated under reduced pressure to give 20 as a colorless oil (2.76 g, 56%); $^1H$ NMR ($CDCl_3$) δ 3.74 (br, 2H), 3.57 (t, 2H), 2.62 (t, 2H), 2.43 (s, 3H), 1.50-1.75 (m, 4H).[18]

(4-Hydroxy-butyl)-methyl-carbamic acid tert-butyl ester, 21.[19]

A solution of 20 (2.76 g, 26.8 mmol) in TEA/MeOH (1:7 v/v, 100 mL) was stirred at 0° C. for 10 min. A solution of di-tert-butyl dicarbonate (8.76 g, 40.2 mmol) in MeOH (20 mL) was added dropwise over 10 min. The mixture was stirred for 1 hr under $N_2$ atmosphere. The temperature was allowed to gradually rise to room temperature, and the solution was stirred overnight. The solution was evaporated under reduced pressure, and the residue was dissolved in $CH_2Cl_2$ and washed with deionized water. The organic layer was separated, dried over anhydrous $Na_2SO_4$, filtered, and concentrated to give a colorless oil 21 that was used in the next step without further purification (4.54 g, 84%); $^1H$ NMR ($CDCl_3$) δ 3.66 (t, 2H), 3.23 (t, 2H), 2.83 (s, 3H), 1.78 (br s, 1H), 1.51-1.60 (m, 4H), 1.44 (s, 9H).[19]

Methanesulfonic acid 4-(tert-butoxycarbonyl-methyl-amino)-butyl ester, 22

To a solution of the alcohol 21 (4.54 g, 22.24 mmol) and TEA (15.5 mL, 111 mmol) in $CH_2Cl_2$ (60 mL) at 0° C., methanesulfonyl chloride (12.73 g, 111 mmol) was added dropwise over 30 min under a $N_2$ atmosphere. The reaction mixture was stirred at 0° C. for 1 hr and was slowly warmed to room temperature and stirred overnight under $N_2$. The reaction mixture was then cooled to 0° C., and a 1 M NaOH solution (500 mL) was added slowly with vigorous stirring. The organic phase was separated and washed with deionized water. The organic phase was again separated, dried over anhydrous $Na_2SO_4$, filtered and concentrated to give the product 22 as a colorless oil that was used in the next step without further purification (6.03 g, 96%); $^1H$ NMR ($CDCl_3$) δ 4.25 (t, 2H), 3.28 (t, 2H), 3.02 (s, 3H), 2.84 (s, 3H), 1.78 (m, 2H), 1.66 (m, 2H), 1.44 (s, 9H).

[4-(4-Amino-butylamino)-butyl]-methyl-carbamic acid tert-butyl ester, 23

Putrescine (9.45 g, 107 mmol) was dissolved in acetonitrile (200 mL) with $K_2CO_3$ (14.79 g, 107 mmol) and stirred under $N_2$. Mesylate 22 (6.03 g, 21.4 mmol) dissolved in acetonitrile (60 mL) was added dropwise over 30 min while stirring under $N_2$. After 30 min, the reaction mixture was brought to reflux and stirred overnight. The reaction mixture was then cooled, solid $K_2CO_3$ was filtered off and the filtrate concentrated in vacuo. The residue was re-dissolved in $CH_2Cl_2$ (200 mL) and washed six times with sat. aqueous $Na_2CO_3$ to remove the unreacted putrescine. The organic layer was then dried over anhydrous $Na_2SO_4$, filtered, and concentrated to give the product 23 as a clear oil that was used in the next step without further purification, yield: 5.31 g (90%); $^1H$ NMR ($CDCl_3$) δ 3.21 (t, 2H), 2.84 (s, 3H), 2.71 (t, 2H), 2.62 (t, 4H), 1.40-1.60 (m, 17H).

tert-Butyl (4-((4-aminobutyl)(tert-butoxycarbonyl) amino)butyl)(methyl)carbamate, 28

To a stirred solution of 23 (5.54 g, 20.3 mmol) and anhydrous $Na_2SO_4$ (23 g, 160 mmol) in 25% MeOH/$CH_2Cl_2$ (500 mL) at room temperature was added salicylaldehyde (2.47 g, 20.3 mmol) dropwise over 5 min, and the reaction was allowed to stir for 1 hour. After $^1H$ NMR showed complete conversion to the imine, the reaction was cooled to 0° C. and di-tert-butyl dicarbonate (4.42 g, 20.3 mmol) was added as a solid. The reaction was then stirred for 45 min at room temperature. The volatiles were then removed under reduced pressure and the residue was re-dissolved in absolute EtOH (400 mL) and cooled to 0° C. A 1 M HCl (30 mL) solution was added dropwise and then the reaction was warmed to room temperature and allowed to stir for 2 hours. After hydrolysis was complete, the volatiles were removed under reduced pressure, and the residue was washed 3 times with deionized water to remove excess salicylaldehyde. The residue was then re-dissolved in $CH_2Cl_2$ and washed 3 times with sat. aq. $Na_2CO_3$ to generate the free base. The free base was then purified by column chromatography $R_f$=0.28 (1% $NH_4OH$/10% MeOH/89% $CH_2Cl_2$) to give a pale yellow oil (3.55 g, 47%). $^1H$ NMR ($CDCl_3$) δ 3.18 (t, 6H), 2.82 (s, 3H), 2.71 (t, 2H), 1.25-1.65 (m, 26H).

Di-tert-butyl(((anthracene-9,10-diylbis(methylene)) bis(azanediyl))bis(butane-4,1-diyl))bis((4-((tert-butoxycarbonyl)(methyl)amino)butyl)carbamate), 29

To a stirred solution of amine 28 (600 mg, 1.61 mmol) in 25% MeOH/$CH_2Cl_2$ (25 mL) was added a solution of anthracene-9,10-dicarboxaldehyde (172 mg, 0.73 mmol) in 25% MeOH/$CH_2Cl_2$ (20 mL). The reaction was then stirred at room temperature under $N_2$ overnight. After complete imine formation was determined by $^1H$ NMR, the solvents were then removed in vacuo and the residue was re-dissolved in 50% MeOH/$CH_2Cl_2$ (25 mL). The solution was then cooled to 0° C. followed by addition of $NaBH_4$ (166 mg, 4.38 mmol) in small portion and the mixture was stirred at room temperature for 2 hours. After complete reduction, the solvents were removed in vacuo and the residue was re-dissolved in $CH_2Cl_2$ and washed three times with aqueous $Na_2CO_3$, then dried over $Na_2SO_4$, filtered, and concentrated in vacuo to give 29 as a yellow oil (505 mg, 73%). $R_f$=0.28 (6% MeOH/0.5% $NH_4OH$/93.5% $CH_2Cl_2$); $^1H$ NMR ($CDCl_3$) δ 8.37 (dd, 4H), 7.53 (dd, 4H), 4.70 (s, 4H), 3.19 (t, 12H), 2.89 (t, 4H), 2.81 (s, 6H), 1.57-1.44 (m, 52H); $^{13}C$ NMR ($CDCl_3$) δ 155.8, 155.6, 132.1, 130.1, 125.7, 124.9, 79.1, 50.4, 46.9, 46.0, 34.1, 28.5, 27.5. HRMS (FAB) m/z calc for $C_{54}H_{88}N_6O_8$ ($M^+$) 949.3119. found 949.6736. Elemental analysis $C_{54}H_{88}N_6O_8$·0.5$H_2O$ theory C, 67.68; H, 9.36; N, 8.77. found C, 67.78; H, 9.09; N, 8.57.

Di-tert-butyl(((((naphthalene-1,4-diylbis(methylene)) bis(azanediyl))bis(butane-4,1-diyl))bis((tert-butoxycarbonyl)azanediyl))bis(butane-4,1-diyl))bis(methylcarbamate), 30

Yellow oil (55%), $R_f$=0.29 (10% MeOH/0.5% $NH_4OH$/89.5% $CH_2Cl_2$); $^1H$ NMR ($CDCl_3$) δ 8.21 (dd, 2H), 7.52 (dd, 2H), 7.71 (s, 2H), 4.22 (s, 4H), 3.19 (t, 12H), 2.81 (s, 3H), 2.75 (t, 4H), 1.31-1.62 (m, 52H); $^{13}C$ NMR ($CDCl_3$) δ 155.8, 155.6, 135.5, 132.2, 125.8, 125.6, 124.4, 79.2, 79.1, 51.8, 49.8, 46.9, 34.1, 28.5, 27.5. Elemental analysis $C_{50}H_{86}N_6O_8$ theory C, 66.78; H, 9.64; N, 9.35. found C, 66.55; H, 9.61; N, 9.13.

Di-tert-butyl(((1,4-phenylenebis(methylene))bis (azanediyl))bis(butane-4,1-diyl))bis((4-((tert-butoxycarbonyl)(methyl)amino)butyl)carbamate), 31

Yellow oil (74%), $R_f$=0.25 (7% MeOH/0.5% $NH_4OH$/92.5% $CH_2Cl_2$); $^1H$ NMR ($CDCl_3$) δ 7.27 (s, 4H), 3.76 (s, 4H), 3.20 (t, 12H), 2.83 (s, 6H), 2.64 (t, 4H), 1.53-1.45 (m, 52H); $^{13}C$ NMR ($CDCl_3$) δ 155.7, 155.5, 138.9, 128.1, 79.0, 53.6, 49.0, 46.9, 34.0, 28.4, 27.3. HRMS (FAB) m/z calc for $C_{46}H_{84}N_6O_8$ (M+H) 849.6351. found 849.6423. Elemental analysis $C_{46}H_{84}N_6O_8$ theory C, 65.06; H, 9.97; N, 9.90. found C, 65.02; H, 9.87; N, 9.69.

$N^1,N^{1'}$-(1,3-phenylenebis(methylene))bis($N^4$-(4-aminobutyl)butane-1,4-diamine) (34a)

Compound 40a (174 mg, 0.21 mmol) was dissolved in EtOH (30 mL) and stirred at 0° C. for 10 min, and then a 4 M HCl solution (12 mL, 48 mmol) was then added dropwise and stirred for 30 min. The temperature was then allowed to rise to room temperature and the solution was then stirred under $N_2$ for four hours. The solvents were then removed in vacuo and the remaining white solid was washed three times with hexanes to remove BHT. The hexanes were then filtered away to give a white solid (80 mg, 24% over 3 steps). $^1H$ NMR ($D_2O$) δ 7.57 (s, 3H), 7.55 (s, 1H), 4.26 (s, 4H), 3.20-3.01 (m, 16H), 1.76 (m, 16H); $^{13}C$ NMR ($D_2O$) δ 134.7, 133.9, 133.8, 133.0, 53.6, 49.8, 49.5, 41.7, 26.8, 25.7. HRMS (FAB) m/z calc for $C_{24}H_{48}N_6$ $(M+H)^+$421.3940. found 421.4013. Elemental Analysis: $C_{24}H_{54}Cl_6N_6$·0.75$H_2O$ theory C, 44.15; H, 8.57; N, 12.87. found C, 44.07; H, 8.57; N, 12.71.

$N^1,N^{1'}$-(1,3-phenylenebis(methylene))bis($N^4$-((4-aminobutyl)amino)butyl)butane-1,4-diamine) (34b)

Compound 40b (130 mg, 0.11 mmol) was dissolved in EtOH (10 mL) and stirred at 0° C. for 10 min, and a 4 M HCl solution (6 mL, 24 mmol) was added dropwise and stirred for 30 min. The temperature was then allowed to rise to room temperature and the solution was stirred under $N_2$ for four hours. The solvents were then removed in vacuo to give a white solid (95 mg, 98%). $^1$H NMR (D$_2$O) δ 7.59-7.57 (m, 4H), 4.30 (s, 4H), 3.17-3.04 (m, 24H), 1.79-1.77 (m, 24H); $^{13}$C NMR 187.9, 134.4, 133.8, 133.7, 132.9, 53.4, 49.6, 49.3, 41.5, 26.6, 25.5. HRMS (FAB) m/z calc for C$_{32}$H$_{66}$N$_8$ (M+H)$^+$563.5410. found 563.5483. Elemental Analysis: C$_{32}$H$_{74}$Cl$_8$N$_8$·0.5H$_2$O theory C, 42.54; H, 8.37; N, 12.40. found C, 42.57; H, 8.63; N, 12.07.

Di-tert-butyl(((1,3-phenylenebis(methylene))bis (azanediyl))bis(butane-4,1-diyl))bis((4-((tert-butoxy-carbonyl)amino)butyl)carbamate) (40a)

In order to maximize the yield, MeOH was dried and distilled prior to this reaction. To a stirred solution of N$^1$/,N$^6$-diboc-homospermidine (566 mg, 1.58 mmol) in 25% MeOH/CH$_2$Cl$_2$ (20 mL) was added a solution of 1,3-benzene dicarboxaldehyde 39 (69.9 mg, 0.52 mmol) in 25% MeOH/CH$_2$Cl$_2$ (15 mL). The reaction was then stirred at room temperature under N$_2$ overnight. After imine formation was complete (by $^1$H NMR), the solvents were removed in vacuo and the residue was redissolved in 50% MeOH/CH$_2$Cl$_2$ (25 mL). The solution was then cooled to 0° C. followed by addition of pre-dried NaBH$_4$ (118 mg, 3.13 mmol) in small portions and the mixture was stirred at room temperature under N$_2$ for 2 hours. The solvents were then removed under reduced pressure and the residue was redissolved in CH$_2$Cl$_2$ and washed three times with aqueous Na$_2$CO$_3$. The organic layer was separated, dried over Na$_2$SO$_4$, filtered, and concentrated in vacuo. After column chromatography (R$_f$=0.25, 25% hexanes/0.1% NH$_4$OH/74.9% THF), compound 40a was isolated as a mixture with BHT and was deprotected without further purification. $^1$H NMR (CDCl$_3$) δ 7.26-7.15 (m, 4H), 3.62 (s, 4H), 3.14 (t, 12H), 2.58 (t, 4H), 1.58-1.27 (m, 16H); $^{13}$C NMR (CDCl$_3$) δ 155.0, 154.5, 139.5, 126.9, 78.1, 66.9, 53.0, 48.2, 45.6, 39.2, 26.8, 25.8, 24.5. Note: The BHT impurity could be avoided by pre-distilling the THF prior to chromatography.

Di-tert-butyl(((1,3-phenylenebis(methylene))bis (azanediyl))bis(butane-4,1-diyl))bis((4-((tert-butoxy-carbonyl)(4-((tert-butoxycarbonyl)amino)butyl) amino)butyl)carbamate) (40b)

To a stirred solution of N$^1$,N$^6$,N$^{11}$-triBoc-homospermine (705 mg, 1.33 mmol) in 25% MeOH/CH$_2$Cl$_2$ (20 mL) was added a solution of 1,3-benzene dicarboxaldehyde 39 (52.3 mg, 0.39 mmol) in 25% MeOH/CH$_2$Cl$_2$ (15 mL). The reaction was then stirred at room temperature under N$_2$ overnight. After imine formation was complete by $^1$H NMR, the solvents were removed in vacuo and the residue was redissolved in 50% MeOH/CH$_2$Cl$_2$ (25 mL). The solution was then cooled to 0° C. followed by addition of NaBH$_4$ (88.5 mg, 2.34 mmol) in small portions and the mixture was stirred at room temperature under N$_2$ for 2 hours. The solvents were then removed under reduced pressure and the residue was redissolved in CH$_2$Cl$_2$ and washed three times with aqueous Na$_2$CO$_3$. The organic layer was separated, dried over Na$_2$SO$_4$, filtered, and concentrated in vacuo. After column chromatography (R$_f$=0.31 (10% MeOH/1% NH$_4$OH/89% CH$_2$Cl$_2$)), compound 40b was isolated as a colorless oil (240 mg, 53%) $^1$H NMR (CDCl$_3$) δ 7.32-7.19 (m, 4H), 3.77 (s, 4H), 3.15 (t, 20H), 2.65 (t, 4H), 1.60-1.44 (m, 78H); $^{13}$C NMR (CDCl$_3$) δ 156.0, 155.5, 140.5, 128.4, 127.8, 126.7, 79.1, 54.0, 49.3, 46.9, 46.6, 40.2, 28.5, 27.4, 26.1. HRMS (FAB) m/z calc for C$_{62}$H$_{11}$N$_8$O$_{12}$ (M+H)$^+$1163.8629. found 1163.8629. Elemental Analysis: C$_{62}$H$_{114}$N$_8$O$_{12}$ theory C, 64.00; H, 9.87; N, 9.63. found C, 64.24; H, 9.96; N, 9.82.

1.14 REFERENCES

All references set forth herein in this document are incorporated by reference herein to the extent that the subject matter therein does not conflict with the existing disclosure.

1. (a) Cullis, P. M.; Green, R. E.; Merson-Davies, L.; Travis, N., Probing the mechanism of transport and compartmentalization of polyamines in mammalian cells. *Chem. Biol.* 1999, 6, 717-729; (b) Seiler, N.; Delcros, J.-G.; Moulinoux, J. P., Polyamine transport in mammalian cells. An update. *Int. J. Biochem.* 1996, 28, 843-861; (c) Seiler, N.; Dezeure, F., Polyamine transport in mammalian cells *Int. J. Biochem.* 1990, 22, 211-218.
2. Casero, R. A. M., L. J., Targeting polyamine metabolism and function in cancer and other hyperproliferative diseases. *Nat. Rev. Drug Discov.* 2007, 6, 373-390.
3. (a) Phanstiel, O.; Price, H. L.; Wang, L.; Juusola, J.; Kline, M.; Shah, S. M., The effect of polyamine homologation on the transport and cytotoxicity properties of polyamine-(DNA intercalator) conjugates. *J. Org. Chem.* 2000, 65, 5590-5599; (b) Wang, L.; Price, H. L.; Juusola, J.; Kline, M.; Phanstiel, O. I., Influence of polyamine architecture on the transport and topoisomerase II inhibitory properties of polyamine DNA-intercalator conjugates. *J. Med. Chem.* 2001, 44, 3682-3691; (c) Wang, C.; Delcros, J.-G.; Biggerstaff, J.; Phanstiel, O., Synthesis and biological evaluation of N1-(anthracen-9-ylmethyl)triamines as molecular recognition elements for the polyamine transporter. *J. Med. Chem.* 2003, 46, 2663-2671; (d) Wang, C.; Delcros, J.-G.; Biggerstaff, J.; Phanstiel, O., Molecular requirements for targeting the polyamine transport system: Synthesis and biological evaluation of polyamine anthracene conjugates. *J. Med. Chem.* 2003, 46, 2672-2682; (e) Wang, C.; Delcros, J.-G.; Cannon, L.; Konate, F.; Carias, H.; Biggerstaff, J.; Gardner, R. A.; Phanstiel, O., Defining the molecular requirements for the selective delivery of polyamine conjugates into cells containing active polyamine transporters. *J. Med. Chem.* 2003, 46, 5129-5138; (f) Kaur, N.; Delcros, J.-G.; Martin, B.; Phanstiel, O., Synthesis and biological evaluation of dihydromotuporamine derivatives in cells containing active polyamine transporters. *Journal of Medicinal Chemistry* 2005, 48, 3832-3839; (g) Gardner, R. A.; Delcros, J.-G.; Konate, F.; Breitbeil, F.; Martin, B.; Sigman, M.; Phanstiel, O., N1-Substituent effects in the selective delivery of polyamine-conjugates into cells containing active polyamine transporters. *J. Med. Chem.* 2004, 47, 6055-6069.
4. Palmer, A. J. W., H. M., The polyamine transport system as a target for anticancer drug development. *Amino Acids* 2010, 38, 415-422.
5. (a) Soulet, D. G., B.; Rivest, S.; Audette, M.; Poulin, R., A fluorescent probe of polyamine transport accumulates into intracellular acidic vesicles via a two-step mechanism. *J. Biol. Chem.* 2004, 279, 49355-49366; (b) Soulet, D. C., L.; Kaouass, M.; Charest-Gaudreault, R.; Audette, M.; Poulin, R., Role of endocytosis in the internalization of spermidine-C(2)-BODIPY, a highly fluorescent probe of polyamine transport. *Biochem. J.* 2002, 367, 347-357.
6. (a) Belting, M.; Persson, S.; Fransson, L.-A., Proteoglycan involvement in polyamine uptake. *Biochem. J.* 1999, 338, 317-323; (b) Belting, M. M., K.; Jonsson, M.; Cheng, F.; Sandgren, S.; Jonsson, S.; Ding, K.; Delcros, J-G.; Fransson, L-A., Glypican-1 is a vehicle for polyamine uptake in mammalian cells: A pivotal role for nirosothiol-derived nitric oxide. *J. Biol. Chem.* 2003, 278, 47181-47189.
7. Delcros, J.-G. T., S.; Carrington, S.; Martin, B.; Renault, J.; Blagbrough, I. S.; Uriac, P., Effect of spermine conjugation on the cytotoxicity and cellular transport of acridine. *J. Med. Chem.* 2002, 45, 5098-5111.
8. (a) Heaton, M. A. F., Wayne F., Methylglyoxal-bis(guanylhydrazone)-Resistant Chinese Hamster Ovary Cells: Genetic Evidence That More Than A Single Locus Controls Uptake. *J. Cell. Physiol.* 1988, 136, 133-139; (b) Mandel, J. L.; Flintoff, W. F., Isolation of mutant mammalian cells altered in polyamine transport. *J. Cell. Physiol.* 1978, 97, 335-344.
9. Bergeron, R. J.; McManis, J. S.; Weimar, W. R.; Schreier, K.; Gao, F.; Wu, Q.; Ortiz-Ocasio, J.; Luchetta, G.; Porter, C.; Vinson, J. R., The role of charge in polyamine analogue recognition. *J. Med. Chem.* 1995, 38, 2278-2285.
10. Phanstiel, O. I.; Kaur, N.; Delcros, J.-G., Structure-activity investigations of polyamine-anthracene conjugates and their uptake via the polyamine transporter. *Amino Acids* 2007, 33, 305-313.
11. (a) Bergeron, R. J.; Feng, Y.; Weimar, W. R.; McManis, J. S.; Dimova, H.; Porter, C. W.; Raisler, B.; Phanstiel, O., A comparison of structure-activity relationships between spermidine and spermine analogue antineoplastics. *J. Med. Chem.* 1997, 40, 1475-1494; (b) Kramer, D. L.; Miller, J. T.; Bergeron, R. J.; Khomutov, R.; Khomutov, A.; Porter, C. W., Regulation of polyamine transport by polyamines and polyamine analogues. *J. Cell. Physiol.* 1993, 155, 399-407; (c) Byers, T. L.; Wechter, R.; Nuttall, M. E.; Pegg, A. E., Expression of a human gene for polyamine transport in chinese hamster ovary cells. *Biochem. J.* 1989, 263, 745-752.
12. Kaur, N.; Delcros, J.-G.; Imran, J.; Khaled, A.; Chehtane, M.; Tschammer, N.; Martin, B.; Phanstiel, O. I., A comparison of chloroambucil- and xylene-containing polyamines leads to improved ligands for accessing the polyamine transport system. *J. Med. Chem.* 2008, 51, 1393-1401.
13. (a) Gahl, W. A.; Pitot, H. C., Reversal by aminoguanidine of the inhibition of proliferation of human fibroblasts by spermidine and spermine *Chem.-Biol. Interact.* 1978, 22, 91-98; (b) Morgan, D. M., Polyamine oxidases and oxidized polyamines. In *Physiology of Polyamines, Bachrach, U.; Heimer, Y. M., Eds. CRC Press: Boca Raton, Fla.*, 1989; Vol. 1, pp 203-229.
14. (a) Flescher, E. B., T. L.; Ballester, A.; Houk, R.; Talal, N., Increased polyamines may downregulate interleukin 2 production in rheumatoid arthritis. *J. Clin. Invest.* 1989, 83, 1356-1362; (b) Flescher, E. B., T. L.; Talal, N., Polyamine oxidation down-regulates IL-2 production by human peripheral blood mononuclear cells. *J. Immunol.* 1989, 142, 907-912; (c) Flescher, E. F., D.; Talal, N., Polyamine-dependent production of lymphocytotoxic levels of ammonia by human peripheral blood monocytes. *Immunol. Lett.* 1991, 28, 85-90; (d) Suzuki, O. M., T.; Katsumata, Y., Determination of polyamine oxidase activities in human tissues. *Experientia* 1984, 40, 838-839.
15. Seiler, N. D., B.; Gosse, F.; Raul, F., Spermine cytotoxicity to human colon carcinoma-derived cells (CaCo-2). *Cell Biol. Toxicol.* 2000, 16, 117-130.
16. Kaur, N.; Delcros, J.-G.; Archer, J.; Weagraff, N. Z.; Martin, B.; Phanstiel, O. I., Designing the polyamine pharmacophore: Influence of N-substituents on the transport behavior of polyamine conjugates. *J. Med. Chem.* 2008, 51, 2551-2560.
17. (a) Casero, R. A.; Celano, P.; Ervin, S. J.; Wiest, L.; Pegg, A. E., High specific induction of spermidine/spermine N1-acetyltransferase in a human large cell lung carcinoma. *Biochem. J.* 1990, 270, 615-620; (b) Fogel-Petrovic, M.; Kramer, D. L.; Vujcic, S.; Miller, J.; McManis, J. S.; Bergeron, R. J.; Porter, C. W., Structural basis for differential induction of spermidine/spermine $N^1$-Acetyltransferase activity by novel spermine analogs. *Mol. Pharmacol.* 1997, 52, 69-74; (c) Coleman, C. S.; Pegg, A. E., Polyamine analogues inhibit the ubiquitination of spermidine/spermine N1-acetyltransferase and prevent its targeting to the proteasome for degradation. *Biochem. J.* 2001, 358, 137-145; (d) Kramer, D. L.; Fogel-Petrovic, M.; Diegelman, P.; Cooley, J. M.; Bernacki, R. J.; McManis, J. S.; Bergeron, R. J.; Porter, C. W., Effects of novel spermine analogues on cell cycle progression and apoptosis in MALME-3M human melanoma cells. *Cancer Res.* 1997, 57, 5521-5527; (e) Barreiro, E. J.; Kummerle, A. E.; Fraga, C. A. M., The methylation effect in medicinal chemistry. *Chem. Rev.* 2011.
18. Kruczynski, A.; Vandenberghe, I.; Pillon, A.; Pesnel, S.; Goetsch, L.; Barret, J.-M.; Guminski, Y.; Le Pape, A.; Imbert, T.; Bailly, C.; Guilbaud, N., Preclinical activity of F14512, designed to target tumors expressing an active polyamine transport system. *Invest. New Drugs* 2011, 29, 9-21.
19. Asaki, T.; Hamamoto, T.; Sugiyama, Y.; Kuwano, K.; Kuwabara, K., Structure-activity studies on diphenylpyrazine derivatives: A novel class of prostacyclin receptor agonists. *Bioorg. Med. Chem. Lett.* 2007, 15, 6692-6704.
20. Kane, B. E.; Grant, M. K. O.; El-Fakahany, E. E.; Ferguson, D. M., Synthesis and evaluation of xanomeline analogs-Probing the wash-resistant phenomenom at the $M_1$ muscarinic acetylcholine receptor. *Bioorg. Med. Chem. Lett.* 2008, 16, 1376-1392.
21. Middleton, R.; Briddon, S.; Cordeaux, Y.; Yates, A.; Dale, C.; George, M.; Baker, J.; Hill, S.; Kellam, B., New fluorescent adenosine $A_1$-receptor agonists that allow quantification of ligand-receptor interactions in microdomains of single living cells. *J. Med. Chem.* 2007, 50, 782-793.
22. (a) Prugh, J.; Birchenough, L.; Egberton, M., A simple method of protecting a secondary amine with tert butyloxycarbonyl (BOC) in the presence of a primary amine. *Synthetic Commun.* 1992, 22, 2357-2360; (b) Laduron, F.; Tamborowski, V.; Moens, L.; Horvath, A.; De Smaele, D.; Leurs, S., Efficient and scalable method for the selective alkylation and acylation of secondary amines in the presence of primary amines. *Org. Process Res. Dev.* 2005, 9, 102-104.
23. (a) Fogel-Petrovic, M.; Shappell, N. W.; Bergeron, R. J.; Porter, C. W., Polyamine and polyamine analog regulation of spermidine/spermine $N^1$-acetyltransferase in MALME-3M human melanoma cells. *J. Biol. Chem.* 1993, 268, 19118-19125; (b) Kramer, D. L.; Vujcic, S.; Diegelman, P.; Alderfer, J.; Miller, J.; Black, J. D.; Bergeron, R. J.; Porter, C. W., Polyamine analogue induction of the p53-p21$^{WAF1/CIP1}$-Rb pathway and $G_1$ arrest in human melanoma cells. *Cancer Res.* 1999, 59, 1278-1286.
24. Mosmann, T., Rapid colorimetric assay for cellular growth and survival: Application to proliferation and cytotoxic assays. *J. Immunol. Methods* 1983, 65, 55-63.
25. Kaur, N.; Delcros, J.-G.; Martin, B.; Phanstiel, O., Synthesis and biological evaluation of dihydromotuporamine derivatives in cells containing active polyamine transporters. *J. Med. Chem.* 2005, 48, 3832-3839.
26. (a) Gerner, E. W. M., F. L.; Goldschmid, S.; Lance, P.; Pelot, D., Rationale for, and design of, a clinical trial targeting polyamine metabolism for colon cancer chemoprevention. *Amino Acids* 2007, 33, 189-195; (b) Chen, Y. W., R. S.; Burns, M. R.; Boorman, D. W.; Klein-Szanto, A., Combination therapy with 2-difluoromethylornithine and a polyamine transport inhibitor against murine squamous cell carcinoma. *Int. J. Cancer* 2006, 118, 2344-2349.

27. (a) Wallick, C. J. G., I.; Thorne, M.; Feith, D. J.; Takasaki, K. Y.; Wilson, S. M.; Seki, J. A.; Pegg, A. E.; Byus, C. V.; Bachmann, A. S., Key role for p27Kip1 retinoblastoma protein Rb, and MYCN in polyamine inhibitor-induced G1 cell cycle arrest in MYCN-amplified human neuroblastoma cells. *Oncogene* 2005, 24, 5606-5618; (b) Hibshoosh, H. J., M.; Weinstein, I. B., Effects of overexpression of ornithine decarboxylase (ODC) on growth control and oncogene-induced cell transformation. *Oncogene* 1991, 6, 739-743.

28. (a) Meyskens Jr, F. L. G., E. W., Development of Difluoromethylornithine (DFMO) as a chemoprevention agent. *Clin. Cancer Res.* 1999, 5, 945-951; (b) Fabian, C. J. K., B. F.; Brady, D. A.; Mayo, M. S.; Chang, C. H.; Ferraro, J. A.; Zalles, C. M.; Stanton, A. L.; Masood, S.; Grizzle, W. E.; Boyd, N. F.; Arneson, D. W.; Johnson, K. A., A Phase II breast cancer chemoprevention trial of oral alpha-difluoromethylornithine: Breast tissue, imaging, and serum and urine biomarkers. *Clin. Cancer Res.* 2002, 8, 3105-3117; (c) Abeloff, M. D. S., M.; Luk, G. D.; Griffin, C. A.; Hermann, J.; Blanc, O.; Sjoerdsma, A.; Baylin, S. B., Phase I trial and pharmacokinetic studies of alpha-difluoromethylornithine—an inhibitor of polyamine biosynthesis. *J. Clin. Oncol.* 1984, 2, 124-130.

29. (a) Seiler, N., Thirty years of polyamine-related approaches to cancer therapy. Retrospect and prospect. Part 2. Structural analogues and derivatives. *Curr. Drug Targets* 2003, 4, 537-564; (b) Gerner, E. W. M., F. L., Polyamines and cancer: old molecules, new understanding. *Nat. Rev. Cancer* 2004, 4, 781-792.

30. Phanstiel, O. A., J. J., Design of polyamine transport inhibitors as therapeutics. In *Polyamine Drug Discovery*, 1 ed.; Casero, R. W., P., Ed. Royal Society of Chemistry: 2011; p 302.

31. American Cancer Society. *Cancer facts & figures* 2012.

32. (a) Basu Roy, U. K. R., Nathaniel S.; Kachel, Karen L.; Gerner, Eugene W., Activated K-RAS increases polyamine uptake in human colon cancer cells through modulation of caveolar endocytosis. *Mol. Carcinogen.* 2008, 47, 538-553; (b) Basuroy, U. K. G., E. W., Emerging concepts in targeting the polyamine metabolic pathway in epithelial cancer chemoprevention and chemotherapy. *J. Biochem.* 2006, 139, 27-33.

33. Covassin, L. D., M.; Charest-Gaudreault, R.; Audette, M.; Bonneau, M.-J.'; Poulin, R., Synthesis of spermidine and norspermidine dimers as high affinity polyamine transport inhibitors. *Bioorg. Med. Chem. Lett.* 1999, 9, 1709-1714.

34. (a) Burns, M. R. C., C. Lance; Vanderwerf, Scott M.; Ziemer, Josh R.; Weeks, Reitha S.; Cai, Feng; Webb, Heather K.; Graminski, Gerard F., Amino acid/spermine conjugates: Polyamine amides as potent spermidine uptake inhibitors. *J. Med. Chem.* 2001, 44, 3632-3644; (b) Weeks, R. S. V., S. M.; Carlson, C. L.; Burns, M. R.; O'Day, C. L.; Cai, F.; Devens, B. H.; Webb, H. K., Novel lysine-spermine conjugate inhibits polyamine transport and inhibits cell growth when given with DEMO. *Exp. Cell Res.* 2000, 261, 293-302.

35. Burns, M. R.; Graminski, G. F.; Weeks, R. S.; Chen, Y.; O'Brien, T. G., Lipophilic lysine-spermine conjugates are potent polyamine transport inhibitors for use in combination with a polyamine biosynthesis inhibitor. *J. Med. Chem.* 2009, 52, 1983-1993.

36. Gardner, R. A.; Kinkade, R.; Wang, C.; Phanstiel, O. I., Total synthesis of petrobactin and its homologues as potential growth stimuli for *Marinobacter hydrocarbonclasticus*, an oil-degrading bacteria. *J. Org. Chem.* 2004, 69, 3530-3537.

37. Azmi, A. S. A., A.; Banerjee, S.; Rangnekar, V. M.; Mohammad, R. M.; Sarkar, F. H., Chemoprevention of pancreatic cancer: Characterization of Par-4 and its modulation by 3,3' diindolylmethane (DIM). *Pharm. Res.* 2008, 25, 2117-2124.

38. Kaur, N.; Delcros, J.-G.; Imran, J.; Khaled, A.; Chehtane, M.; Tschammer, N.; Martin, B.; Phanstiel, O. I., A comparison of chloroambucil- and xylene-containing polyamines leads to improved ligands for accessing the polyamine transport system. *J. Med. Chem.* 2008, 51, 1393-1401.

39. Structure-activity Investigations of Polyamine-anthracene Conjugates and their Uptake via the Polyamine Transporter. Phanstiel, IV, O.; Kaur, N.; Delcros, J-G. *Amino Acids*, 2007, 33, No. 2, 305-313.

The teachings of all cited references are incorporated in their entirety to the extent they are not inconsistent with the teachings herein. U.S. Patent Pubs 20090069441, 20090155265, and 20070213397 are further incorporated by reference herein for background information, as well as teachings on pharmaceutical compositions, formulations, dosages and modes of administration that can be applied to the compounds and compound combinations described herein.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

What is claimed is:

1. A compound of the following the formula:

$$R'HN-(CH_2)_x-NH-(CH_2)_y-NH-CH_2-R-CH_2-NH-(CH_2)_{xx}-NH-(CH_2)_{yy}-NHR'' \quad (I)$$

wherein R is selected from the group consisting of anthracene, naphthalene, and benzene;

wherein x, xx, y, and yy are independently selected from the group consisting of 3 and 4;

or a pharmaceutically acceptable salt thereof; wherein R' and R" are independently selected from the group consisting of methyl, ethyl, propyl, isopropyl, and butyl.

2. The compound of claim 1, wherein R' and R" are each methyl.

3. The compound of claim 1, wherein x, xx, y, and yy are each 4.

4. The compound of claim 1, wherein x, xx, y, and yy are each 3.

5. The compound of claim 1, wherein R' and R"=methyl, wherein x, xx, y, and yy are each 4, and wherein R=anthracene.

6. The compound of claim 1, wherein R' and R"=methyl, wherein x, xx, y, and yy are each 4, and wherein R=naphthalene.

7. The compound of claim 1, wherein R' and R"=methyl, wherein x, xx, y, and yy are each 4, and wherein R=benzene.

8. A compound of the following the formula:

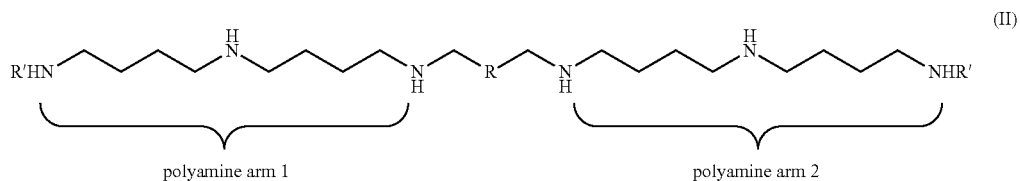

wherein R is selected from the group consisting of anthracene, naphthalene, and benzene; and
or a pharmaceutically acceptable salt thereof; wherein each R' is independently selected from the group consisting of methyl, ethyl, propyl, isopropyl and butyl.

9. The compound of claim 8, wherein each R' is methyl.
10. The compound of claim 8, wherein R=anthracene.
11. The compound of claim 8, wherein R=naphthalene.
12. The compound of claim 8, wherein R=benzene.
13. A compound of the following the formula:

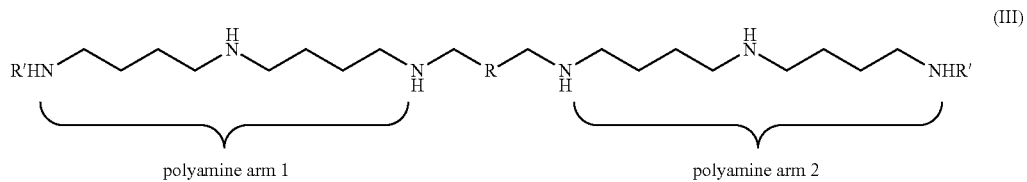

wherein R is selected from the group consisting of anthracene (6b), naphthalene (7b), and benzene (8b); and
wherein R' is methyl;
or a pharmaceutically acceptable salt thereof.

14. The compound of claim 13, wherein R=naphthalene.
15. The compound of claim 13, wherein R=anthracene.
16. The compound of claim 13, wherein R=benzene.
17. A method for treating a disorder characterized by unrestrained cell proliferation and/or differentiation, wherein the method comprises administering to a subject a composition comprising a compound of claim 1 in an amount effective to reduce an amount of cell proliferation or differentiation, wherein the disorder is breast cancer, leukemia or melanoma.

* * * * *